(12) United States Patent
Port et al.

(10) Patent No.: US 7,780,953 B2
(45) Date of Patent: *Aug. 24, 2010

(54) **COMPOSITIONS MAGNETIC PARTICLES COVERED WITH *GEM*-BISPHOSPHONATE DERIVATIVES**

(75) Inventors: Marc Port, Deuil la Barre (FR); Claire Corot, Lyons (FR); Isabelle Raynal, Saint Maur des Fosses (FR); Olivier Rousseaux, Senlis (FR)

(73) Assignee: Guerbet, Villepinte (FR)

( * ) Notice: Subject to any disclaimer, the term of this patent is extended or adjusted under 35 U.S.C. 154(b) by 1123 days.

This patent is subject to a terminal disclaimer.

(21) Appl. No.: 10/739,400

(22) Filed: Dec. 19, 2003

(65) Prior Publication Data

US 2004/0253181 A1 Dec. 16, 2004

(30) Foreign Application Priority Data

Dec. 20, 2002 (FR) .................................. 02 16410

(51) Int. Cl.
*A61B 5/055* (2006.01)
*A61B 5/05* (2006.01)
*A01N 57/18* (2006.01)

(52) U.S. Cl. ..................... 424/9.32; 424/9.3; 424/9.36; 600/410; 514/141

(58) Field of Classification Search ................ 424/9.3, 424/9.32, 9.322, 9.323, 9.34, 9.341, 9.36; 600/410; 514/141

See application file for complete search history.

(56) References Cited

U.S. PATENT DOCUMENTS

| 4,120,890 A | * | 10/1978 | Blum et al. ................... 562/21 |
| 4,329,241 A | | 5/1982 | Massart |
| 4,440,646 A | | 4/1984 | Budnick |
| 5,928,958 A | * | 7/1999 | Pilgrimm ................... 436/526 |
| 6,514,481 B1 | * | 2/2003 | Prasad et al. ............... 424/9.32 |

FOREIGN PATENT DOCUMENTS

| FR | 2 461 521 | 2/1981 |
| GB | 1 1435 295 | 11/1973 |
| WO | 97 01760 A | 1/1997 |
| WO | WO 01/74337 A1 | * 10/2001 |

OTHER PUBLICATIONS

Lefebure, S. et al., J. Materials Research, 1998, 13 (10), p. 2975-2981.*
Portet, D. et al., Drug Development Research, 2001, 54, p. 173-181.*
Massart, R., "Preparation of Aqueous magnetic Liquids in Alkaline and Acidic Media", IEEE Transactions on Magnetics, 17:2 (1981), 1247-48.
Fauconnier et al., "Adsorption of gluconic and citric acids on magnemite particles in aqueous medium", Progr. Colloid Polym Sci. 100 (1996), 212-16.
Tronc et al., "Surface effects on magnetically coupled "gamma-Fe203" colloids", 28 (1986), 525-28.
Roger et al., "Some biomedical applications of ferrofluids", European Physical Journal Applied Physics 5:3 (1999), 321-23.
Portet et al., Nonpolymeric coatings of iron oxide colloids for biological use as magnetic resonance imaging contrast agents Journal of Colloid and Interface Science, 238:1 (2001), 37-42.
Massart et al., "Syntheses en milieu alcalin de magnetite colloidale: controle du rendement et de la taille des particules", Journal de Chimie Physique 84:7/8 (1987), 967-973.
Sahoo et al., Alkyl phosphonate/phosphate coating on magnetite nanoparticles: a comparison with fatty acids, Langmuir, 17 (2001), 7907-7911.
Fauconnier et al., "Synthesis of aqueous magnetic liquids by surface complexation of maghemite nanoparticles", Journal of Molecular Liquids, 83 (1999), 233-242.
Tronc et al., "Magnetic behaviour of gamm-Fe203 nanoparticles by Mössbauer spectroscopy and magnetic measurements", Hyperfine Interactions, 95 (1995), 129-148.
Vayssieres et al., "Size tailoring of magnetite particles formed by aqueous precipitation: an example of thermodynamic stability of nanometric oxide particles", 205 (1998), 205-212.

* cited by examiner

*Primary Examiner*—Michael G Hartley
*Assistant Examiner*—Leah Schlientz
(74) *Attorney, Agent, or Firm*—Jacobson Holman PLLC

(57) ABSTRACT

The invention relates to a composition comprising acid magnetic particles (p) based on an iron compound, the acid magnetic particles (p) being complexed by one or more gem-bisphosphonate compounds, of formula I:

X-L-CH(PO₃H₂)₂      (I)

in which:
L represents an organic group connecting the X group to the gem-bisphosphonate group —CH(PO₃H₂)₂;
X represents a chemical group capable of reacting with a biovector; all or some of the X groups of the particles optionally being coupled to a biovector. The invention relates, also to a process for the preparation of the compositions and their use, in particular as contrast products for Magnetic Resonance Imaging (MRI).

40 Claims, No Drawings

COMPOSITIONS MAGNETIC PARTICLES COVERED WITH GEM-BISPHOSPHONATE DERIVATIVES

The invention relates to compositions of magnetic particles covered with molecules comprising, on the one hand, a gem-bisphosphonate group bonded to the surface of the particle and, on the other hand, a reactive group capable of covalently bonding a targeting entity called a biovector. The invention relates also to their process of preparation and their use in particular as contrast products for nuclear Magnetic Resonance Imaging (MRI).

MRI permits the visualisation of internal organs in living beings and therefore constitutes a powerful guide and auxiliary in diagnostics, medical treatment and surgery.

The administration of contrast products helps to improve the resolution of the images obtained by that technique and the precision of diagnosis.

Thus, the contrast effect may be accentuated by the presence, in the environment of the organs subjected to examination, of various magnetic species, for example paramagnetic, ferromagnetic or superparamagnetic species.

Paramagnetic substances comprise specific metals, such as iron, manganese, gadolinium in the ionic or organometallic state. Ferromagnetic contrast substances generally comprise magnetic aggregate particles of micrometric or sub-micrometric size, that is to say, not less than 100-200 nm, for example particles of ferrites, including in particular magnetite ($Fe_3O_4$), maghemite ($\gamma$-$Fe_2O_3$) and other magnetic mineral compounds of transition elements which behave like permanent magnets. Superparamagnetic particles are normally very small particles of ferrite, including in particular magnetite ($Fe_3O_4$), maghemite ($\gamma$-$Fe_2O_3$) and other magnetic mineral compounds of transition elements, having a size of less than approximately 100-150 nm. Unlike ferromagnetic particles, superparamagnetic particles no longer behave like small autonomous magnets owing to the fact that their size is smaller than a critical value, that is to say, they are aligned in a preferential direction only when they are subjected to an external magnetic field. Superparamagnetic particles advantageously have a higher effective density compared with ferromagnetic particles.

In order to obtain colloidal solutions of magnetic particles, which are also referred to as ferrofluids hereinafter and which are stable in a physiological medium, it is necessary to condition the surface of the magnetic particles.

Generally, the magnetic particles used in medical imaging are covered with macromolecules, such as carbohydrates, such as dextran, proteins, such as albumin, or synthetic polymers, such as methacrylates and organosilanes. The syntheses enabling that type of particle to be obtained are generally carried out in accordance with the so-called <<de Molday>> process (Reference: Robert S. Molday and D. Mackenzie; *J. of Immunological Methods* (1982), 52, pp. 353-367) and require laborious and expensive purification processes.

In many biomedical applications of magnetic particles, it is necessary to couple the particles to a molecule of specific affinity, so that the particles bond specifically to the target cells and to tissue. This recognition is often ensured by the formation of an affinity complex between a ligand (biovector) fixed to the particle and a receptor at the surface of the target cell or of a tissue. This molecule of specific affinity may be either adsorbed directly at the surface of the particles or bonded by a covalent bond.

In general, the covalent grafting of the specific affinity molecule onto a macromolecule requires prior chemical activation, for example by oxidation, in order to generate fixation sites on the macromolecule.

However, the number of fixation sites generated on the macromolecule is generally difficult to control and, consequently, the later grafting of a specific affinity molecule cannot be controlled.

The control of the amount of specific affinity molecule grafted is important for modulating the affinity of the final solution of particles relative to the target, but also for modulating the pharmacokinetics, the biodistribution and optionally the metabolism, the excretion and innocuousness of these particles. In addition, from an industrial point of view, it is advantageous to be able to minimise the amount of specific affinity molecule, the cost of which is generally very high.

Furthermore, the reactive groups at the surface of the macromolecule that have not reacted with the specific affinity molecule are capable of bringing about toxic reactions in vivo.

Likewise, the grafting of a specific affinity molecule by chemisorption is generally difficult to control from a physico-chemical point of view and, moreover, is much less stable in a biological medium. In addition, chemisorption brings about an equilibrium with a free fraction of the specific affinity molecule. This free fraction is detrimental to MRI contrast.

Magnetic particles covered with low-molecular-weight organic molecules have also been described to date.

The document *J. of Coll. And Interf. Science* 2001, 238, pp. 37-42 teaches that the covering of magnetic particles with organic molecules comprising a bisphosphonate portion enables objects that are small (less than 15 nm) and stable over a wide pH range to be obtained.

However, the measurement of the hydrodynamic size of the particles covered with bisphosphonate compounds by PCS (Photon Correlation Spectroscopy) described in that document requires a prior filtration step on 100-nm filters in order to remove the aggregates and to isolate only the particles of small hydrodynamic size. Therefore, that measurement does not reflect the real hydrodynamic size of the particles obtained, which is in fact much larger.

In addition, the purification of magnetic particles covered with gem-bisphosphonate compounds by the process described in that document requires the use of a step of dialysis or treatment by resins, which is found to be laborious, poorly reproducible and very difficult to exploit industrially. It will be remembered that gem-bisphosphonates are —CH($PO_3H_2$)$_2$ groups.

That process therefore permits control neither of the grafting of gem-bisphosphonate compounds to the surface of magnetic particles nor of the hydrodynamic size of the resulting particle, without having recourse to laborious purification processes. Furthermore, that document neither describes nor suggests coupling specific targeting entities to particles covered with bisphosphonate compounds, and in particular gem-bisphosphonates, for specific biomedical applications, which makes their use highly unsuitable for this targeting.

The hydrodynamic diameter, in the context of the present invention, refers to the diameter of the particle in solution surrounded by its hydration layer, as determined by light diffusion according to the PCS technique (Photon Correlation Spectroscopy: reference: R. Pecora—*J. of Nanoparticle Research* (2000), Vol. 2, pp. 123-131).

The publication WO 97/01760 describes magnetic particles covered with dimercaptosuccinic acid (DMSA) that are coupled to a specific targeting entity, annexin, via the thiol groups of DMSA.

However, in normal pH and ionic strength conditions, the thiol groups of DMSA that are present at the surface of the particle have a tendency to oxidise and to form disulphide bridges, which leads to the formation of aggregates. The result is a large hydrodynamic size and a high degree of polydispersion.

The grafting of annexin also requires, beforehand, regeneration of the thiol groups by reduction of the disulphide bridges.

Finally, the grafting of annexin is poorly controlled. Therefore, after coupling, it is found to be necessary to deactivate the residual thiol groups by reaction with BSA (Bovine Serum Albumin) in order to avoid toxic reactions in vivo or the later aggregation of the particles obtained.

There is therefore still a need to obtain particles that are efficient in respect of a specific diagnosis and that, at the same time, exhibit a low degree of polydispersion and are stable.

It has now been found that it is possible to control both the grafting of functionalised gem-bisphosphonate compounds onto magnetic particles and the coupling of the resulting particles to biovectors thanks to the combined use of the gem-bisphosphonate compounds and acid magnetic particles. This double control has the advantage of permitting, in particular, the control of the hydrodynamic size of the resulting particles, namely the acid magnetic particles (p) grafted by gem-bisphosphonate compounds, regardless of whether or not they are coupled to biovectors. The invention thus relates in particular to:

the acid particles onto which the gem-bisphosphonates are grafted, those particles, once grafted, being capable of binding to at least one biovector;

the particles grafted by gem-bisphosphonates and coupled to at least one biovector.

In this context, it has been found that the process for obtaining such magnetic particles comprises a limited number of steps and is both simple to implement and reproducible. Furthermore, it does not require laborious purification processes and is characterised by very good yields.

In the context of the present invention, "acid magnetic particle" means magnetic particles of the same type as those present within so-called "acid" ferrofluids, which are known from the prior art but the association of which with gem-bisphosphonates has been neither described nor suggested.

These "acid" ferrofluids, like the "alkaline" ferrofluids have been widely described in the literature, in particular in the publication Massart et al., C. R. Acad. Sc. Paris, t. 291, Jul. 7, 1980, Série C and IEE, *Transactions on Magnetics,* 1981, vol. MAG-17, no 2, p. 1247.

The acid magnetic particles of acid ferrofluids are generally described as having protonated hydroxyl sites at the surface, in an acid medium.

In contrast, the magnetic particles of alkaline ferrofluids are described as generally having sites complexed by OH⁻ ions in a basic medium.

This representation in terms of sites in fact corresponds to a model which has also been confirmed by various works showing that acid and base magnetic particles behave like weak polyacids and/or polybases.

Advantageously, the inventors have shown that, unlike "alkaline" ferrofluids, "acid" ferrofluids are very stable and do not exhibit a particle aggregation phenomenon, which results in a better control of the hydrodynamic size of the precursor (that is to say, of the non-grafted particle) and subsequently of the particles grafted by gem-bisphosphonate compounds, then, where appropriate, of the said particles coupled to biovectors, without a laborious purification step.

Surprisingly, the inventors have also shown that it is possible to obtain very good covering of the magnetic particles by gem-bisphosphonate compounds, it being possible for each protonated hydroxyl site at the surface of the acid magnetic particle to be potentially grafted by a molecule of gem-bisphosphonate complexing agent. This interaction advantageously enables the surface of the particle to be masked homogeneously, which in particular prevents later recognition of the particle by the immune system.

In particular, the inventors have also found a process enabling the hydrodynamic size of acid magnetic particles to be reduced and consequently enabling magnetic particles of very small size to be obtained. Advantageously, the controlled grafting of these particles by gem-bisphosphonate agents, optionally followed by likewise controlled coupling with biovectors, permits the production of final magnetic particles of small hydrodynamic size without a laborious purification step, and therefore ultimately provides a robust, reproducible and therefore industrially applicable preparation process.

The inventors have also studied the complexing of acid magnetic particles (p) by compounds comprising, on the one hand, an X group capable of covalently bonding a biovector and, on the other hand, a diphosphonate group in place of the gem-bisphosphonate group.

They have thus obtained stable particles, which is already a marked improvement over the prior art, but coupling to a biovector is significantly less efficient than with a gem-bisphosphonate. In particular, when a diphosphonate compound HOOC—CH$_2$—N(CH$_2$(PO$_3$H$_2$))$_2$ is used, for reasons which are not entirely clear, the particles have a rate of coupling with the biovector which is twice as low as with a gem-bisphosphonate. The result is therefore that the cost of producing magnetic particles grafted by diphosphonates and coupled to biovectors would be much higher.

The object of the present invention is therefore to propose compositions of magnetic particles grafted in a controlled manner by gem-bisphosphonate derivatives and optionally coupled in a controlled manner, via those derivatives, to species of the specific targeting entity type (biovector).

More specifically, the object of the invention is also to provide compositions of that type that are stable in suspension, in particular in a biological medium, and that advantageously have a controlled hydrodynamic size, especially a small hydrodynamic size.

The object of the present invention is also to propose a process for the preparation of those compositions.

According to a first aspect, the invention relates to a composition comprising acid magnetic particles (p) based on an iron compound, the acid magnetic particles (p) each being complexed by one or more gem-bisphosphonate compounds, of formula (I):

in which:

L represents an organic group connecting the X group to the gem-bisphosphonate group —CH(PO$_3$H$_2$)$_2$;

X represents a chemical group capable of reacting with a biovector; all or some of the X groups of the particles (p) optionally being coupled to a biovector.

The person skilled in the art will understand the expression "each being complexed" to mean that the composition may also comprise magnetic particles (p) not complexed by compounds of formula (I), this being principally for random distribution reasons and/or owing to the process for the preparation of the composition, which process is described hereinafter.

The composition is in the form of a stable aqueous solution of nanoparticles.

In these compositions, the rate of complexing of the compound (I) on the particles is higher than 70%, and preferably higher than 80, 90, 95%, it being understood that the expression "rate of complexing" in the present description refers preferably to the amount of compounds of formula (I), in relation to the amount of protonated sites present on the acid magnetic particles (p).

It is in particular preferable for the acid magnetic particles (p) to be complexed on at least 90% of their protonated sites by compounds of formula (I), which advantageously leads to a good covering of the particle, capable in particular of ensuring good stability of the particle, preventing recognition of the particle by the immune system and making the optional later coupling with a biovector more efficient.

Magnetic Particle (P)

In the context of the present description, "particles based on an iron compound" means particles, all or some of which are constituted by an iron derivative, generally comprising iron (III), generally an iron oxide or hydroxide.

As a general rule, some or all of the acid magnetic particles (p) are composed of iron hydroxide; hydrated iron oxide ferrites; mixed iron oxides, such as mixed iron oxides of cobalt, nickel, manganese, beryllium, magnesium, calcium, barium, strontium, copper, zinc, or platinum; or a mixture thereof.

In the context of the present invention, the term "ferrite" means iron oxides of the general formula $[xFe_2O_3, yMO_z]$, where M denotes a metal magnetisable under the effect of a magnetic field, such as Fe, Co, Ru, Mg, Mn, it optionally being possible for the magnetisable metal to be radioactive.

Preferably, the acid magnetic particles (p) of the compositions of the invention comprise a ferrite, especially maghemite ($\gamma Fe_2O_3$) and magnetite ($Fe_3O_4$), or also mixed ferrites of cobalt ($Fe_2CoO_4$) or of manganese ($Fe_2MnO_4$).

In this context, very particular preference is given to acid magnetic particles (p), all or some of which, and preferably most of which, are composed of maghemite or magnetite or of a mixture thereof.

The acid magnetic particles (p) of the compositions according to the invention have at their surface hydroxyl sites protonated in an acid medium, which correspond more precisely to the species $Fe-OH_2^+$ resulting from a very strong interaction between an $Fe^{3+}$ ion at the surface of the particle and an acid water molecule ($H_3O^+$). These protons may be regarded as constituting the particle according to the works of J. Lyklema et al., *Materials Science Research*, 1984, 17, pp. 1-24. The percentage of protonated sites on an acid particle is typically from 1.3 to 2.5% (mole of sites/mole of iron).

According to a particularly preferred variant, the acid particles (p) are superparamagnetic.

The magnetic particles (p) then have a hydrodynamic diameter of from 5 to 300 nm, preferably from 5 to 60 nm, and more preferably from 5 to 30 nm.

Preferably, the composition of the invention is a suspension of acid magnetic particles (p) which advantageously has, where appropriate, a concentration suitable for the formation of a stable colloidal solution (stable aqueous suspension of nanoparticles), that is to say, in general, a concentration of magnetic particles (p) of from 2 µmoles $L^{-1}$ to 4 moles $L^{-1}$, expressed as the total number of moles of metal ions.

Compounds of Formula (I)

The compounds of formula (I) according to the invention comprise a gem-bisphosphonate group which ensures that the compound of formula (I) is fixed to the surface of the acid magnetic particle.

More precisely, the inventors have demonstrated that each gem-bisphosphonate group interacts with a single protonated hydroxyl site at the surface of the acid particle.

The compounds of formula (I) of the invention comprise a linker (L) enabling the gem-bisphosphonate group and the reactive entity X, capable of ensuring the covalent grafting of a biovector, to be connected and/or spaced from one another.

Preferably, the linker L represents a divalent group.

Preferably, the linker L is selected from an aliphatic; alicyclic; alicyclic-aliphatic; aromatic; aromatic-aliphatic group, it optionally being possible for the aliphatic, alicyclic and aromatic groups to be substituted by a methyl, hydroxy, methoxy, acetoxy, amido group, or a chlorine, iodine or bromine atom;

a group -$L_1$-NHCO-$L_2$ where $L_1$ and $L_2$ are either identical or different and represent an aliphatic; alicyclic; aromatic; alicyclic-aliphatic or aromatic-aliphatic group, it optionally being possible for the said groups to be substituted by a methyl, hydroxy, methoxy, acetoxy, amido group or a chlorine, iodine or bromine atom.

An aliphatic group in the context of the present invention means a linear or branched hydrocarbon chain preferably comprising from to 16 carbon atoms, and even more preferably from 1 to 6 carbon atoms. Examples thereof are, in particular, methyl, ethyl, propyl, isopropyl, butyl, tert-butyl, isobutyl, pentyl and hexyl radicals.

The term "alicyclic" means a cyclic hydrocarbon chain preferably comprising from 3 to 8 carbon atoms. By way of example, mention will be made in particular of cyclopropyl and cyclohexyl.

The term "aromatic" represents a mono- or polycyclic aromatic hydrocarbon group preferably comprising from 5 to 20 carbon atoms, and even more preferably from 6 to 18. Examples thereof are, in particular, phenyl and 1- or 2-naphthyl radicals. According to one particular variant, an "aromatic" group in the context of the invention may incorporate one or more hetero atoms, such as sulphur, oxygen or nitrogen. In this particular case, the "aromatic" group denotes a mono- or polycyclic heteroaromatic group.

The "aliphatic-alicyclic" and "aliphatic-aromatic" groups represent aliphatic chains corresponding to the above-mentioned definition that are substituted by an alicyclic or aromatic group, respectively, such as defined above. In particular, benzyl may be mentioned by way of example of an aliphatic-aromatic group.

According to a preferred variant, L represents an optionally substituted phenylene group, it being possible for the X and gem-bisphosphonate groups to be in the ortho, meta or para position.

According to one particularly preferred embodiment, L represents a substituted or unsubstituted aliphatic group, and more preferably a group —$(CH_2)_p$—, where p is an integer from 1 to 5.

According to another preferred embodiment, L represents a group $L_1$-CONH-$L_2$ and more preferably a group —$(CH_2)_n$—NHCO—$(CH_2)_m$— where n and m represent an integer from 0 to 5.

The X end of the gem-bisphosphonate compound of formula (I) is chosen in such a manner that it is capable of reacting and forming a covalent bond with a group present on the biovector. For more information concerning these coupling processes reference may be made in particular to the work *Bioconjugate techniques*, Greg T. Hermanson, 1995, Publisher: Academic, San Diego, Calif.

There may be mentioned as preferred X groups, in particular:
- —COOH,
- —NH$_2$, —NCS, —NH—NH$_2$, —CHO, alkylpyrocarbonyl (—CO—O—CO-alk), acylazidyl (—CO—N$_3$), iminocarbonate (—O—C(NH)—NH$_2$), vinylsulphuryl (—S—CH═CH$_2$), pyridyldisulphuryl (—S—S-Py), haloacetyl, maleimidyl, dichlorotriazinyl, halogen,
- the groups —COOH and —NH$_2$ being especially preferred.

The term <<alk>> in the context of the present description means a C$_1$-C$_6$ alkyl radical, the term <<Py>> for its part meaning a pyridyl radical.

The maleimidyl radical denotes a cyclic radical of formula

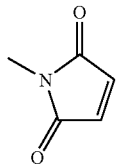

The dichlorotriazinyl radical denotes a radical of formula:

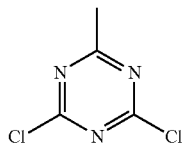

Among the halogen groups, mention may in particular be made of chlorine, bromine, fluorine and iodine, chlorine and bromine being particularly preferred.

In the context of the present invention, "haloacetyl" means an acetyl radical CH$_3$—CO—, one of the hydrogen atoms of which is substituted by a halogen atom, said halogen atom being as defined above.

Preferably, X represents a group —COOH or —NH$_2$ and L represents a substituted or unsubstituted aliphatic group, better still a group —(CH$_2$)$_p$—, where p is an integer from 1 to 5.

The compound of formula (Ia)

HOOC—(CH$_2$)$_2$—CH(PO$_3$H$_2$)$_2$ (Ia)

is most particularly preferred.

According to another preferred embodiment, L represents a group L$_1$-CONH-L$_2$ and more preferably a group —(CH$_2$)$_n$—NHCO—(CH$_2$)$_m$— where n and m represent an integer from 0 to 5 and X represents —COOH or —NH$_2$.

Of course, also falling within the context of the invention is the coupling of the X group and of the biovector in an indirect manner, that is to say via a homobifunctional or heterobifunctional reagent. By way of illustration the homo-bifunctional reagent, glutaraldehyde may be suitable for carrying out the coupling, for example, of a group X═—NH$_2$ with a group —NH$_2$ of the biovector.

According to a preferred variant of the invention, the X groups form a covalent bond L$_3$ with the biovector, of type
—CONH—, —COO—, —NHCO—, —OCO—, —NH—CS—NH—, —C—S—, —N—NH—CO—, —CO—NH—N—, —CH$_2$—NH—, —N—CH$_2$—, —N—CS—N—, —CO—CH$_2$—S—, —N—CO—CH$_2$—S—, —N—CO—CH$_2$—CH$_2$—S—, —CH═NH—NH—, —NH—NH═CH—, —CH═N—O— or —O—N═CH—, or corresponding to the formulae below:

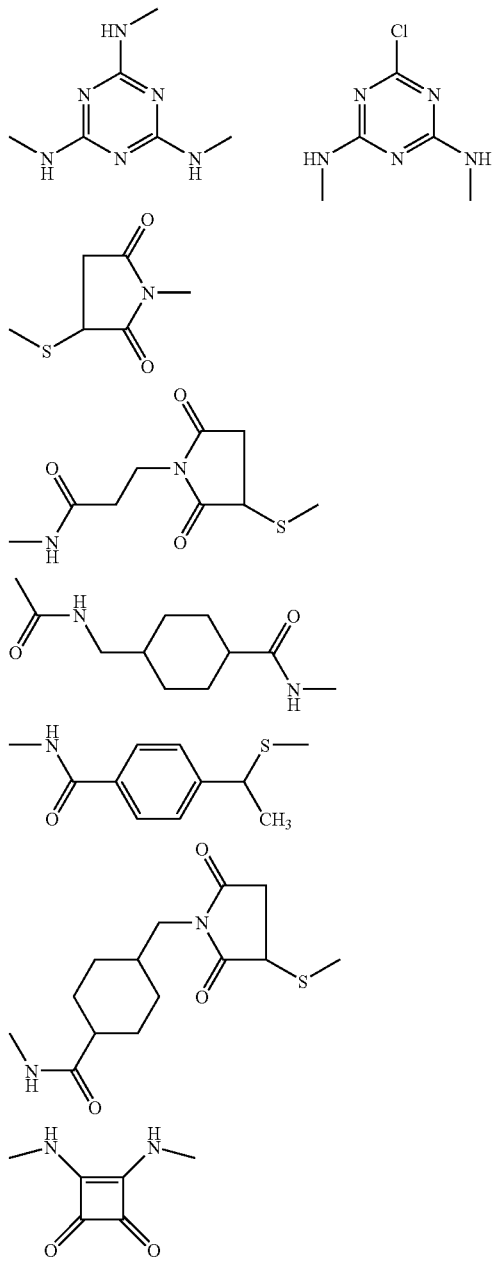

According to one particular embodiment, it is possible to envision coupling two biovectors on the same X group via a bond of type:

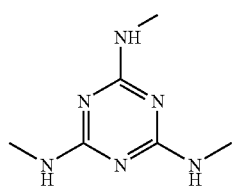

The protonated sites of the acid magnetic particles (p) according to the invention can be complexed by at least two compounds of formula (I) having identical or different structures.

According to a preferred embodiment, the magnetic particles (p) are complexed by one or more molecules of two compounds of formula (I) having different structures, in particular having different X groups. This advantageously permits the subsequent grafting of biovectors having groups capable of reacting with different X groups.

According to a preferred embodiment, all or some of the X groups of the gem-bisphosphonate compound are coupled to a biovector.

The invention thus also relates to a composition (which can be used as a contrast product for MRI) comprising a stable aqueous suspension of acid nanoparticles (p) in which at least 90% of the protonated sites are complexed by one or more identical or different gem-bisphosphonate compounds of formula (I):

$$X\text{-}L\text{-}CH(PO_3H_2)_2 \quad (I)$$

in which all or some of the X groups are coupled to at least one biovector.

The expression "all or some" means that not all the X groups of the gem-bisphosphonate compound are necessarily coupled to a biovector, but that the degree of coupling is sufficient for the desired diagnostic specificity to be obtained with the biovectors used. It is also specified that if several X groups and/or several biovectors are used, the X groups and/or the biovectors can be identical or different.

The particle thus vectorized is written:

$$(BRANCH)_r\text{-}ACID\ PARTICLE \quad (III)$$

in which r represents the number of branches grafted per particle and BRANCH is defined by:

$[((BIOVECTOR)\text{-}L_3)_s\text{-}L\text{-}CH(PO_3H_2)_2]$, $L_3$ being a covalent bond as defined above resulting from the coupling of the X group of the compound of formula (I) and of the biovector, optionally via a homobifunctional or heterobifunctional reagent; s represents the number of biovectors coupled per X group, and can in particular be equal to 1, 2 or 3.

Biovector

In the context of the present invention "biovector" preferably means a specific targeting entity (generally a ligand), that is to say having a specific affinity for a given target tissue and/or biological receptor and/or transporter and/or biological matrix.

There are many receptor/ligand affinity couples, and the invention as defined may be readily applied by the person skilled in the art to various ligands capable of forming an affinity pair with a target receptor, such as the antibody/antigen, lectin/polysaccharide, biotin/avidin or nucleic acids (+ and − strand) couples, it being understood that the ligand may be coupled via a covalent bond either directly to the X end of the compound of formula (I), or indirectly via a bifunctional reagent.

By extension, in the context of the present description, the term "biovector" can also cover organic molecules having a pharmacological and/or cytotoxic activity or, more generally, pharmacophores useful in methods of therapeutic or prophylactic treatment.

In the context of the present invention, the term "pharmacophore" covers organic molecules with pharmacological and/or cytotoxic activity, and also structural analogs thereof, the latter possibly having a pharmacological and/or cytotoxic activity.

In the context of the present description, a "biovector" denotes, by extension, biocompatible molecules which are markedly hydrophilic in nature, such as amino alcohols.

As preferred biovectors, mention can in particular be made of proteins, optionally recombinant or mutated, glycoproteins, lectins, biotin, vitamins, pteroic or aminopteroic derivatives, antifolic and folic acid derivatives, antibodies or antibody fragments, peptides and derivatives thereof, monosaccharides or polysaccharides, avidin, (membrane or nuclear) receptor substrates or inhibitors, phospholipids, steroids and analogs thereof, oligonucleotides, ribonucleic acid sequences, deoxyribonucleic acid sequences, hormones or hormone-like substances, amino acids, organic molecules with pharmacological activity, pharmacophores, proteins, optionally recombinant or mutated, antibodies or antibody fragments, amino alcohols, phospholipid derivatives, pharmacophores; antifolic and folic acid derivatives, integrin-targeting agents or MMP-targeting agents being particularly preferred.

The biovectors, including in particular the antibodies and the pharmacophores, can be optionally functionalized so as to be able to react with the X groups and to form a covalent bond, preferably of type —CONH—, —COO—, —NHCO—, —OCO—, —NH—CS—NH—, —C—S—, —N—NH—CO—, —CO—NH—N—, —CH$_2$—NH—, —N—CH$_2$—, —N—CS—N—, —CO—CH$_2$—S—, —N—CO—CH$_2$—S—, —N—CO—CH$_2$—CH$_2$—S—, —CH═NH—NH—, —NH—NH═CH—, —CH═N—O— or —O—N═CH—, or corresponding to the formulae below:

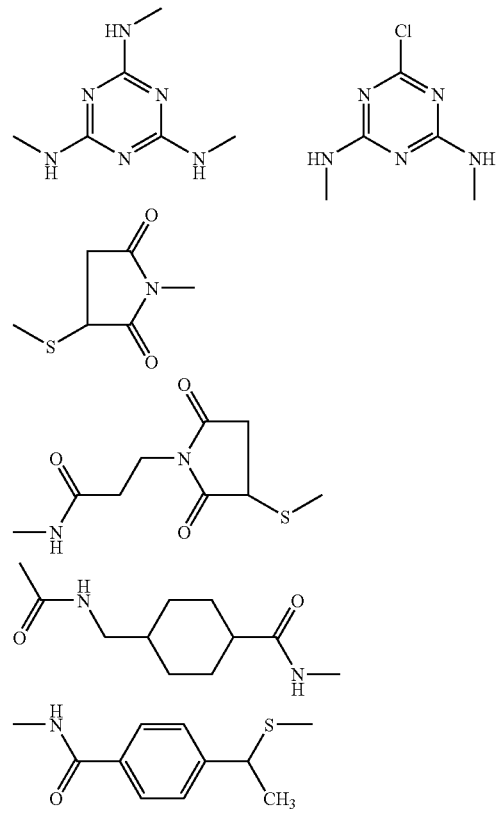

-continued

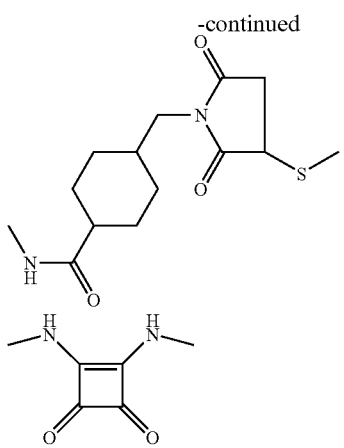

The term "folic acid derivatives and antifolic derivatives" denotes molecules obtained by functionalization of at least one chemical group of folate or of pteroic acid such that they may form a covalent bond with the X groups, in particular of the type such as those mentioned above. By way of example of functionalization, mention may in particular be made of etherification of a hydroxyl group, esterification or amidation of a carboxylate group, or the modification and/or introduction of substituents on the (2-aminopyrimidine) structural motif) and more particularly on the (2-aminopyrimidine) structural motife present in the aminopterinic and pteroic derivatives. By way of preferred examples of folate derivatives, mention may more particularly be made of those described in the article by M. P Costi—*Current Drug Targets* (2001), vol 2, p. 135-166.

By way of preferred examples of "phospholipid" derivatives, mention may be made of phosphatidylserine, phosphatidylethanolamine, phosphatidylcholine, phosphatidylinositol or sphingomyelin derivatives or ceramide derivatives, the term "derivative" here meaning that the molecules are functionalized in such a way that they are capable of reacting covalently with the X groups described above, in particular with X=—COOH or —NH$_2$.

In the context of the present description, "peptide derivative" means a peptide derived from amino acids which may or may not be natural, the native structure of which has been chemically modified by functionalization of certain chemical groups, in such a way that the resulting peptide is capable of reacting covalently with the X groups, for example by modification of a peptide bond. By way of indication, a peptide derivative can denote a polypeptide, a pseudo-peptide, a retropeptide, a peptidomimetic, a cyclic peptide, enzyme-inhibiting peptides, agonist peptides or antagonist peptides. By way of preferred examples, mention may be made of the functionalized peptides used in nuclear medicine (Reference: S. Liu and D. Scott Edwards; *Topics in Current Chemistry* (2002), 222, p 259-278) and Okarvi, *Nuclear Medicine Communication,* 1999, 20: 1093-1112) and the inhibitors or substrates of proteases, in particular of metalloproteases.

A particular class of biovectors are the highly hydrophilic molecules such as amino alcohols or amino polyethylene glycols. These amino alcohols are particularly useful for obtaining final magnetic particles which are sufficiently hydrophilic in terms of aqueous stability and of biocompatibility, and also for modulating the pharmacokinetics and the biodistribution.

Among the amino alcohols, preference is particularly given to those corresponding to formula (II) below:

in which $R_1$ and $R_2$ are identical or different and represent an aliphatic hydrocarbon chain comprising from 2 to 6 carbon atoms, preferably substituted by 6 to 10 hydroxyl groups, or else by 4 to 8 hydroxyl groups when $R_1$ and/or $R_2$ is interrupted by an oxygen atom.

In this context, the amino alcohols for which $R_1$ represents a group —(CH$_2$)—(CHOH)$_4$—CH$_2$OH or —(CH$_2$)—CHOH—CH$_2$OH and $R_2$ a group —CH$_2$—(CHOH)$_4$—CH$_2$OH are generally preferred.

Among the aminopolyethylene glycols, preference is particularly given to the compounds of formula (II) in which $R_1$ and $R_2$, which are identical or different, represent H, an alkyl group or a polyethylene glycol chain of formula —CH$_2$—(CH$_2$—O—CH$_2$)$_k$—CH$_2$OR$_3$ in which k ranges from 2 to 100, and $R_3$ is selected from H, alkyl or —(CO)alk, the term "alkyl" or "alk" denoting a linear or branched aliphatic hydrocarbon group having approximately from 1 to 6 carbon atoms in the chain.

Examples of aminopolyethylene glycols are in particular the compounds O-(2-aminoethyl)-O'-methylpolyethylene glycol 1100, O-(2-aminoethyl)-O'-methylpolyethylene glycol 2000 and O-(2-aminoethyl)-O'-methylpoly-ethylene glycol 750.

According to a particular variant of the invention, where appropriate, biovectors which are different in nature are coupled via the X groups to the surface of magnetic particles (p). In this context, it is most particularly preferred to couple two different biovectors to each acid magnetic particle (p).

According to one embodiment, a "mixed" coupling is carried out between an amino alcohol and a biovector which is different in nature, that is to say which exhibits either a specific affinity for a given target, or a pharmacological and/or cytotoxic activity, so as to modify the biodistribution of the final product.

It is preferred that 1 to 100% of the X groups of the gem-bisphosphonate compounds be coupled to at least two identical or different biovectors. By way of example, 30% of the X groups can be coupled to a biovector B1, 30% to a biovector B2 and 30% coupled to a biovector B3, B1, B2 and B3 being different.

While it is possible to envision coupling 100% of the X groups present at the surface of the acid magnetic particles (p) to biovectors, a coupling yield which limits the increase in hydrodynamic size of the final particle, while at the same time making it possible to ensure effective specific targeting, is generally preferred.

Thus, according to a preferred embodiment of the invention, 1 to 70%, in particular 1 to 50%, of the X groups of the compounds of formula (I) are coupled, and in particular when the biovectors are identical.

According to a variant of the invention which is also preferred, when the biovectors are different, in particular when it involves an amino alcohol and a biovector different in nature, 1 to 100% of the X groups of the compounds of formula (I) are then coupled.

More generally, a mixed coupling can, for example, be used with biovectors which are different but capable of specifically targeting the same pathology, such as peptides having different sequences which are capable of targeting various metalloproteases (MMPS) overexpressed in a pathological cancerous or cardiovascular region.

Various biovectors, which can particularly be used in the context of the invention are now described more precisely in three fields:

A) cardiovascular
B) oncology
C) inflammatory and degenerative diseases.

A) Cardiovascular Field and Atheroma Plaque at Risk

Various biological systems/mechanisms present in cardiovascular diseases, in particular those associated with atheroma plaques, are preferred targets for the contrast or therapeutic agents according to the invention, in particular the system involving metalloproteases (MMPs), the thrombus system, the annexin V system.

It is known that matrix metalloproteinases (MMPs) or matrixins, are enzymes which have the property of degrading the protein components of the extracellular matrix. This extracellular matrix which surrounds cells and tissues consists of proteins such as collagen. The MMPs are classified into 3 groups: gelatinases (type IV collagenases), stromelysins and interstitial collagenases.

MMPs are overexpressed in atheroma plaques. In the cardiovascular field, many studies indicate that MMPs are involved in the remodeling of the extracellualr matrix in the plaque. With regard to atheroma plaques, in a nonexhaustive manner, at least eight MMPs are overexpressed therein:

| Enzyme | MMP reference |
|---|---|
| Interstitial collagenase | MMP-1 |
| Gelatinase A | MMP-2 |
| Gelatinase B | MMP-9 |
| Stromelysin-1 | MMP-3 |
| Matrilysin | MMP-7 |
| Macrophage elastase | MMP-12 |
| Collagenase-3 | MMP-13 |
| Membrane-type-MMP MT-MMP-1 | MMP-14 |

MMP1 and MMP3 are particularly described in Johnson J et al., Activation of Matrix-degrading Metalloproteinases by Mast Cell Proteases in Atherosclerotic Plaques, *Arterioscl. Thromb. Vasc. Biol.* 1998; 18:1707-1715.

The invention thus relates to vectorized nanoparticles of formula (III) in which the biovector is an agent capable of inhibiting at least one MMP, in particular an MMP inhibitor, for applications in the cardiovascular field. According to a preferred embodiment, the inhibitor is a derivative of Ilomastat or a peptide as exemplified later. Preference will also be given to MMP inhibitors selected from those described in *Current Medicinal Chemistry*, 2001, 8, 425-474; Chem. Rev, 1999, 99, 2735-2776. Use may in particular be made of MMP inhibitors referred to as TIMPs, recalled in DDT vol 1, No 1, January 1996, Elsevier Science, 16-17; *Bioconjugate Chem*, 2001, 12, 964-971.

For the thrombus, it is known that:
the GpIIb/IIIa receptor is expressed on activated platelets (it is already used in therapeutics as a target for antiplatelet agents);
fibrin is associated with thrombosis.

More precisely, as regards the thrombus, the involvement of GpIIb/IIIa glycoproteins on activated platelets has been demonstrated. The platelets are anuclear fragments of bone marrow megakaryocytes which play a pivotable role in the processes of atherosclerosis and of thrombosis. The most commonly used conventional antiplatelet medicinal products are aspirin, ticlopidine and clopidogrel. Knowledge of the molecular mechanisms resulting in platelet aggregation has made it possible to develop a new family of molecules directed against the platelet receptor fibrinogen, the integrin GPIIb/IIIa. The major advantage compared to the antagonists mentioned above is that the final step of platelet activation is blocked, independently of the route of activation of the platelets. Since platelet-platelet interaction is critical for formation of the thrombus, binding of fibrinogen (which forms bridges between the platelets) to the GP IIb/IIIa complex is a key event in hemostasis and thrombosis. When the platelets are activated, the GP IIb/IIIa glycoprotein receptors which are at the surface of the platelet membranes undergo a modification of their spatial conformation and can then bind molecules of fibrinogen soluble in the plasma, and calcium. The fibrinogen is linked between the platelets via $Ca^{2+}$-fibrinogen bonds forming a network in which the blood cells will be trapped. The thrombin, by converting the fibrinogen to fibrin, tightens the mesh of this net. This aggregation will lead to the formation of a thrombus in the damaged area. Many studies have therefore been carried out in order to identify, on the GP IIb/IIIa receptor, the ligand interaction sites. The GP IIb/IIIa complex is an important membrane-bound heterodimeric glycoprotein complex in platelets (approximately 50 000 copies per platelet).

At least two series of peptides, corresponding to amino acid sequences naturally present in human fibrinogen, are known to inhibit the binding of adhesion macromolecules to the GPIIb/IIIa receptor: the sequence Arg-Gly-Asp (RGD) and the Lys-Gln-Ala-Gly-Asp-Val gamma chain.

The sequence Arg-Gly-Asp (RGD) was initially identified as the adhesion sequence of fibronectin, an integrin which plays an important role in platelet-platelet and platelet-vessel interactions after its release by platelets. This sequence is also present in fibrinogen, von Willebrand factor and vitronectin (role in fibrinolysis and binding to vessels).

The GPIIb/IIIa complex recognizes this sequence which inhibits the binding of fibronectin, of fibrinogen, of von Willebrand factor and vitronectin on platelets. All these ligands contain at least one RGD sequence; while fibrinogen contains two thereof per half-molecule. In vivo, fibrinogen is the main ligand due to its high concentration in the plasma.

The invention thus relates to vectorized particles (III):
in which the biovector is capable of targeting the GpIIb/IIIa receptor;
in which the biovector is capable of targeting fibrin, in particular through peptides selective for the fibrin monomers in order to differentiate the fibrin from the soluble fibrinogen molecule.

The invention relates in particular to products (III) in which the biovector comprises an RGD motif, for cardiovascular applications.

Use may, for example, be made of peptides described in WO 2001/9188, U.S. Pat. No. 6,521,211, U.S. Pat. No. 6,403, 056, Seminars in nuclear medicine, 1990, 52-67, Nucear Medicine and Radiology, 28, 2001, 515-526, the apcitide Acutect from the company Diatide.

B) Oncology Field

The specific imaging obtained by virtue of the present invention is aimed at obtaining, according to one embodiment, labeling of neoangiogenesis, specific targeting of tumor cells or alterations in the extracellular matrix, not obtained with known techniques. Various biological systems (or mechanisms) associated with tumor development are preferred targets for the contrast or therapeutic agents according to the invention: the system involving compounds capable of binding to folate receptors, the system involving MMPs, the system involving growth factors involved in angiogenesis.

According to one embodiment, the invention relates to products (III) in which the biovector is a derivative capable of targeting a folate receptor, this biovector being capable of providing specific recognition of tumor cells. Use will in particular be made, as biovector, of folic derivatives of formula (E) written: BIOVECTOR:

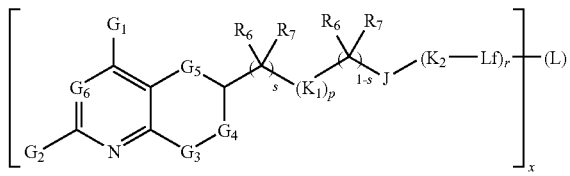

in which:

a) G1 is selected independently from the group consisting of: halo, $R_f2$, $OR_f2$, $SR_f3$, $NR_f4$ $R_f5$; preferably, G1 is $NH_2$ or OH;

b) G2 is selected independently from the group consisting of: halo, $R_f2$, $OR_f2$, $SR_f3$, and $NR_f4$ $R_f5$;

c) G3 and G4 represent divalent groups selected independently from the group consisting of —($R_f6'$) C═, —N═, —($R_f6'$) C($R_f7'$)-, —N($R_f4'$)-;

preferably, G3 is —N═ (folic acid) or —CH— (compounds described later: CB3717, raltitrexed, MAI) when the ring comprising G3 is aromatic, and G3 is —NH— or —CH2- (compounds described later: AG-2034, lometrexol) when the ring comprising G3 is nonaromatic;

preferably, G4 is —CH— or —C(CH3)- when the ring comprising G3 is aromatic, and —CH2- or —CH(CH3)- when the ring comprising G3 is nonaromatic;

e) G5 is absent (compound pemetrexed) or selected from —($R_f6'$) C═, —N═, —($R_f6'$) C($R_f7'$)-, —N($R_f4'$)-;

f) The ring J is a possibly heterocyclic aromatic 5- or 6-membered ring, it being possible for the atoms of the ring to be C, N, O, S;

vii) G6 is N or C (compound described later: 3-deaza-ICI-198,583);

h) K1 and K2 are selected independently from the group consisting of —C($Z_f$)—, —C($Z_f$)O—, —OC($Z_f$)—, —N($R_f4''$)-, —C($Z_f$)—N($R_f4$), —N($R_f4''$)—C($Z_f$), —O—C(Z)—N($R_f4''$)-, —N($R_f4''$)-C($Z_f$)—O—, N($R_f4''$)-C($Z_f$)—N($R_f5''$)-, —O—, —S—, —S(O)—, —S(O)_2—, —N($R_f$ 4")S(O)2-, —C($R_f$ 6")($R_f$ 7")—, —N(C═CH)—, —N(CH_2—C═CH)—, C1-C12 alkyl and C1-C12 alkoxy; Zf is O or S; preferably, K1 is —N($R_f4''$)- or —C($R_f6''$)($R_f7''$)- with $R_f''4$, $R_f6''$, $R_f7''$ being H; A2 possibly being covalently bonded to an amino acid;

i) $R_f1$ is selected from the group consisting of: H, halo, C1-C12 alkyl and C1-C12 alkoxy; $R_f2$, $R_f3$, $R_f4$, $Rf4'$, $R_f4''$, $R_f5$, $R_f5'''$, $R_f6''$ and $R_f7''$ are selected independently from the group consisting of: H, halo, C1-C12 alkyl, C1-C12 alkoxy, C,—C, 2 alkanoyl, C,—C, 2 alkenyl, C1-C12 alkynyl, (C1-C12 alkoxy)carbonyl and (C,—C, 2 alkylamino)carbonyl;

j) $R_f6$ and $R_f7$ are selected independently from the group consisting of: H, halo, C1-C12 alkyl, C1-C12 alkoxy; or $R_f6$ and $R_f7$ together form O═;

k) $R_f6'$ and $R_f7'$ are selected independently from the group consisting of: H, halo, C1-C12 alkyl, C1-C12 alkoxy; or $R_f6'$ and $R_f7'$ together form O═;

l) Lf is a divalent linkage which includes, where appropriate, a natural amino acid or a natural poly(amino acid), bonded to K2 or to K1 via its alpha-amino group via an amide bond;

m) n, p, r and s are independently 0 or 1.

The formula (E) includes the tautomeric forms, for example compounds in which G1 is OH, SH or NH.

For the compounds of the invention in which at least one of the groups K1, K2, $R_f1$, $R_f2$, $R_f3$, $R_f4$, $R_f4'$, $R_f4''$, $R_f5$, $R_f5''$, $R_f6$, $R_f7''$, $R_f6$, $R_f7$, $R_f6'$ and $R_f7'$ comprises a hydrogen atom or an alkyl, alkoxy, alkylamino, alkanoyl, alkenyl, alkynyl, alkoxycarbonyl or alkylaminocarbonyl group, the group preferably comprises 1 to 6 carbon atoms (C1-C6), more preferably 1 to 4 carbon atoms (C1-C4).

As regards MMPs in the oncology field, it is known that MMPs have two distinct functions:

a) they contribute to tumor dissemination by destroying the extracellular matrix;

b) they create an environment which promotes the growth and the angiogenesis of primary tumors and metastasized tumors.

The MMPs expressed in the main human tumors are in particular the following:

breast cancer: MMP-1,2,3,7,9,11,13,14;
colorectal cancer: MMP-1,2,3,7,9,11;
lung cancer: MMP-2,3,7,9,11,14;
prostate cancer: MMP-1,2,3,7,9.

There is a frequent correlation between the state of tumor progression and the level of expression of MMPs. In general, malignant tumors express a greater amount of MMP than benign tumors.

The invention thus relates to products (III) in which the biovector is an MMP inhibitor, for applications in the oncology field. According to preferred embodiments, use will be made of inhibitors selected from those described in *Current Medicinal Chemistry*, 2001, 8, 425-474; *Chem. Rev*, 1999, 99, 2735-2776. Use may in particular be made of MMP inhibitors referred to as TIMPs, recalled in DDT vol 1, No 1, January 1996, Elsevier Science, 16-17; *Bioconjugate Chem*, 2001, 12, 964-971.

As regards angiogenesis, studies have shown that angiogenesis is a prognostic factor in diverse tumors, in particular breast cancer, kidney cancer, prostate cancer, colon cancer and brain cancer, and also melanoma.

The invention thus relates to products (III) in which the biovector is capable of targeting an angiogenesis marker.

It has been shown that certain endothelial growth factors are tumor specific. Endothelial cells, which constitute the inner vessel wall, show no natural tendency to proliferate in normal adults. On the other hand, in pathological situations, for example during the development of tumors or the formation of metastases, the increased needs in oxygen and in nutritive supplies are transported by an increase in local irrigation. The tumors thus derive, to their benefit, a new vascular network, a process known as angiogenesis.

Vascular endothelial cell growth factor (VEGF) is a powerful and selective angiogenic growth factor. It acts by stimulating at least three receptors on the extracellular membrane: VEGFR-1 (Flt-1), VEGFR-2 (Flk-1/KDR) and NP-1. VEGFs receptors belong to the large RTK (tyrosine-kinase receptor) family. These proteins of the integrin family have an extracellular region capable of binding ligands, a transmembrane domain and a cytoplasmic region carrying the tyrosine kinase activity. In the case of VEGFRs, the kinase domain is interrupted by a short sequence specific to each receptor.

The invention thus relates to products (III) in which the biovector is an agent capable of binding to angiogenic receptors present at the surface of endothelial cells.

Use may in particular be made of biovectors (in particular peptides obtained by phage display) described in documents WO 01/012809, WO 01/83693, WO 02/057299 (peptides of 8 amino acids targeting VEGFR3); *Nuclear Medicine Communications* (1999), 20, *Pharmacological Review*, 179, 206, 2000; *Journal of Biological Chemistry*, 2000, 275, 13588-13596; *Journal of Biological Chemistry*, 2002, 277, 45, 43137-43142; *J. Mol. Biol*, 2001, 316, 769-787; *Biochemistry*, 1998, 37, 17754-17772; *Chem. J. Biochem. Mol. Biol,* 2000, 16, 803-806. Use may in particular be made of (i) inhibitors of the VEGF-related enzyme activity, such as quinazoline, aminothiazole or anthranilamide compounds, (ii) compounds which are VEGF antagonists, in particular small molecules such as dibenzothiophenes and molecules of documents JP2001-353075, JP2000-395413, antibodies. Use may also be made of biovectors of document U.S. Pat. No. 6,610,269, which describes many agents for targeting receptors overexpressed in the case of antiogenesis.

It is also known that the integrin αvβ3 is hardly expressed in the vascular system, but is overexpressed in tumor cells (final-stage glioblastoma, ovarian carcinoma melanoma). αvβ3 takes part in angiogenesis at various stages: αvβ3 regulates endothelial cell adhesion to the matrix, it transmits signals to the cell nuclei and is a receptor which is pro-angiogenic by cooperating with the endothelial cell growth factor receptor (VEGFR-2, flk). αvβ3, acting with membrane-type metalloproteinase-1 (MT1-MMP), is responsible for activation of the metalloproteinase-2 of the matrix at the surface of the cells. The blocking of this receptor, but also of αvβ5, with RGD peptides or with antibodies induces apoptosis of the cells. αvβ5, like αvβ5, is involved especially in the proliferative phase of angiogenesis. Many matrix proteins have a common sequence: Arg-Gly-Asp (referred to as RGD), which has been identified as the site of interaction with certain integrins. A large number of antiogenesis inhibitors comprising this RGD sequence have thus been developed.

The invention thus relates to products (III) in which the biovector is an RGD peptide suitable for applications in oncology.

For the RGD peptides targeting αvβ3, the inventors prefer biovectors for inhibiting angiogenesis exhibiting a high affinity for αvβ3 (in order to prevent binding of matrix proteins) but a low affinity for αIIbβ3. In fact, it has been shown that αIIbβ3 antagonists can cause adverse bleeding problems. The inventors prefer in particular antagonists having a cyclic RGD peptide sequence which is more stable to enzyme degradation and better affinity and selectivity, the conformation of the peptide being maintained in a favored position due to rotation restriction.

More precisely, after a structure-activity analysis of the RGD peptides, the inventors prefer most particularly, in order to be under conditions favorable to maintaining affinity for αvβ3, cyclic RGD peptides in order to prevent degradation by enzymes (exopeptidase and endopeptidase), with quite a short ring in order for it to be more rigid (5-amino acid ring preferable to a 6-amino acid ring), with an amino acid in the D configuration. The distance between the β-carbons of aspartic acid and of arginine is particularly less than 6.6 Å in order to have greater selectivity for αvβ3 than for αIIbβ3 (the site of which is large than that of αvβ3). A hydrophobic amino acid close to the aspartic acid also promotes better selectivity. Such a structure is optimal for correct exposure of the hydrophobic and hydrophilic groups in the receptor site. The inventors prefer in particular the peptide cyclo(Arg-Gly-Asp-Dphe-Val), also referred to as cyclo(RGDfV), the lower-case letters indicate a D configuration for the corresponding amino acid. It exhibits an $IC_{50}$ of nanomolar (2-2.5 nM). This peptide is particularly advantageous for the side amine group of lysine which can react with an FR derivative. The synthesis thereof is described in X. Dai, Z. Su, J. O. Liu; *Tetrahedron Letters* (2000), 41, pp 6295-6298.

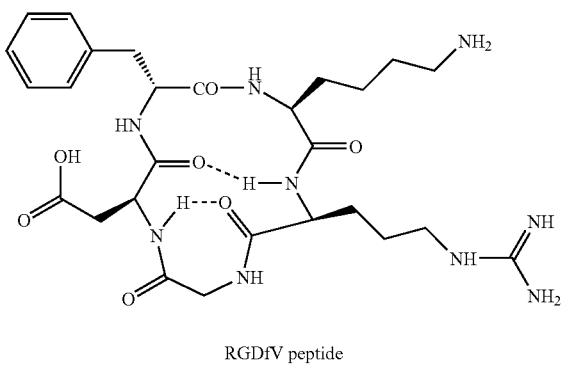

RGDfV peptide

It permits the coupling to USPIOs (functionalized particles) which are in particular COOH—, squarate- or isothiocyanate-functionalized. The inventors have had to overcome the technical difficulties associated with the choice of protection of the amino acids, and with the choice of the coupling medium.

Use may also be made of compounds having a conformation with restricted flexibility, these peptides having good affinity and selectivity for αvβ3:

Peptides in which the RGD motif is placed between two cysteines, the activity for αvβ3 increasing, for example (cyclo(CRGDC));

peptides in which the RGD group is not in the ring, but is bordered by two rings, at least one of which was formed by a disulfide bridge between 2 cysteines (WO 02/26776).

Use may also be made of:

polypeptide biovectors chosen such that they interact in vivo with at least one enzyme, in particular MMP, this interaction resulting in stronger binding with a target protein;

biovectors comprising an enzyme cleavage site, the cleavage resulting in a conformational modification;

biovectors derived from antibodies, such as LM609 (*Nature Medicine*, vol 4, 5, May 1998, 623)

biovectors which mimic RGD peptides, having a structure of quinolone or benzodiazepine type.

The invention also relates to products (III) in which the biovector is a peptidomimetic of the RGD peptide, suitable for applications in oncology. Use may be made of:

peptides with substitution of one or two peptide bonds by thioamide bonds (CSNH) or by keto methylene groups ($COCH_2$) provided that the substitutions do not induce any important conformation change;

peptides (EMD 121974, also called Cilengitide: cyclo (RGDf-N(Me)V), which exhibit an N-methylation of each of the amino acids of the cyclic peptide (RGDfV), this peptide exhibiting very high affinity ($IC_{50}$=0.58 nM) and very great selectivity (1500 times greater than for αIIbβ3);

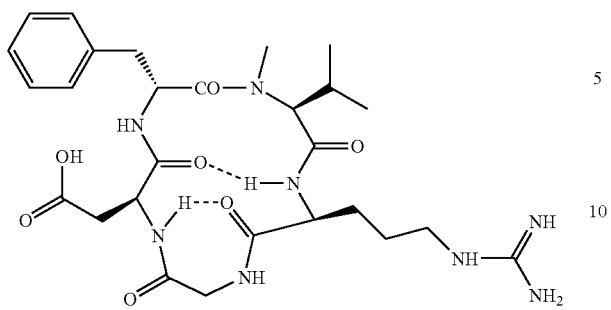

peptides having the following sequence: cyclo(Xaa-Yaa-GD-Mamb), the Mamb group being N-aminomethylbenzoic acid. It is demonstrated that DXaa-N-MeArg peptides are very active antagonists of αIIbβ3, whereas LXaa-Arg antagonists are selective for αvβ3;

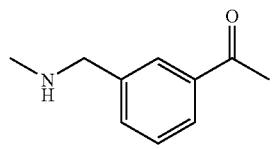

Mamb the cyclic peptide (RGDD(tBuG)Mamb) exhibiting very high affinity for αvβ3 ($IC_{50}$=0.6 nM versus 14 μm for αIIbβ3) due to the hydrophobic nature of the amino acid neighboring the aspartic acid and to the Mamb group which makes the peptide less flexible in aqueous solution;

the peptide XJ735 (DUPONT) having the group: cyclo (ARGD-Mamb). This makes it possible to inhibit the binding of fibrinogen to the αvβ3 receptor ($IC_{50}$=70 nM) but does not block other integrins (αvβ5, α5β1);

peptides obtained by introducing various groups in place of Dphe-Val (or fV) into the reference peptide RGDfv.

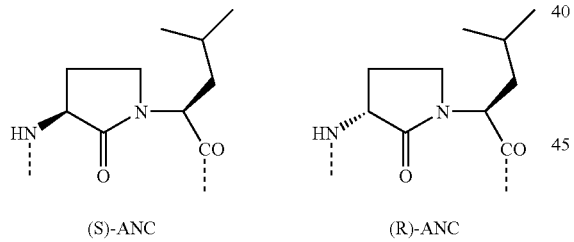

(S)-ANC        (R)-ANC

-continued

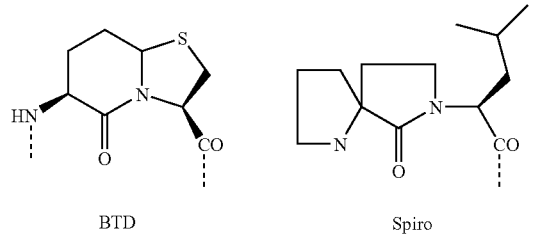

BTD        Spiro

These groups were synthesized in order to mimic the βII' folding, but also to reduce the flexibility in the γ-rotation region. The most active agent is the cyclo (RGD-(R)-ANC) ($IC_{50}$=0.8 nM). It is also possible to introduce therein sugars X in place of these two amino acids (fv) in the sequence cyclo (RGDX) (Lohof E. et al; *Angew. Chem. Int.* Ed. Engl. (2000), 39 (15), pp. 2761-2764);

peptides with introduction of a double bond into the ring (Kawaguchi, et al, *Biochemical and Biophysical Research Communications* (2001), 288(3), pp. 711-717);

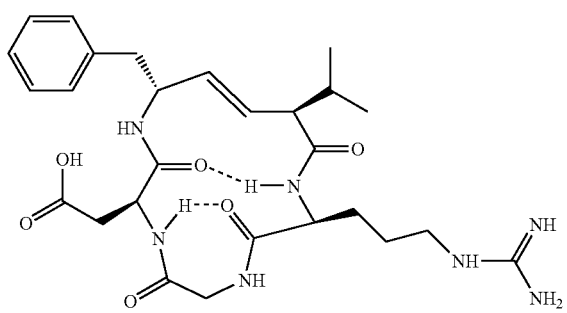

peptides described in Chemlibrary.bri.nrc.ca.

The invention also relates to products (III) in which the biovector is a nonpeptide molecule targeting the integrin αvβ3, suitable for applications in oncology. Use may be made of the compounds in the following table, the nanomolar affinity of which has been demonstrated.

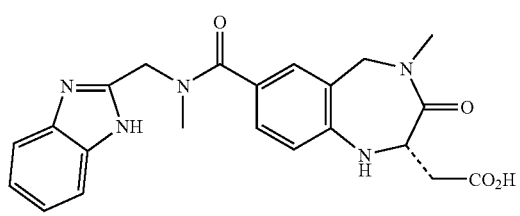

Compound
Benzodiazepine - Benzozepine and derivatives

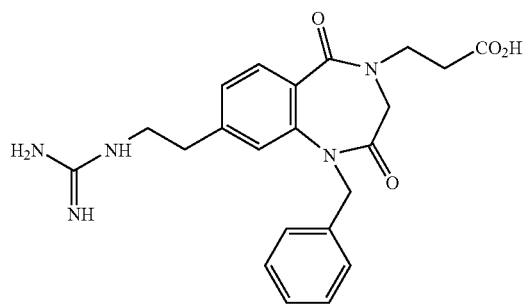

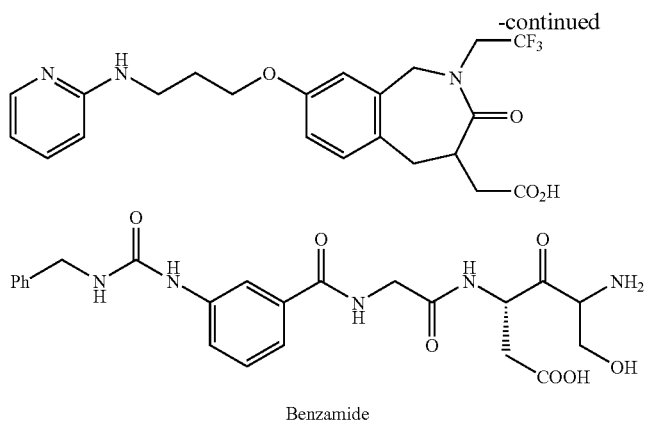
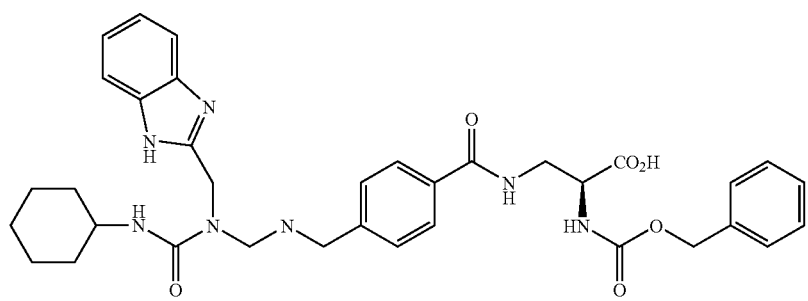
Benzamide
SCH221153
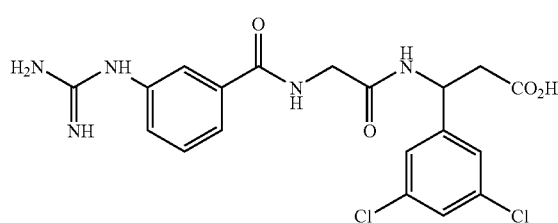
SC 68448
and other compounds of document WO 01/97861
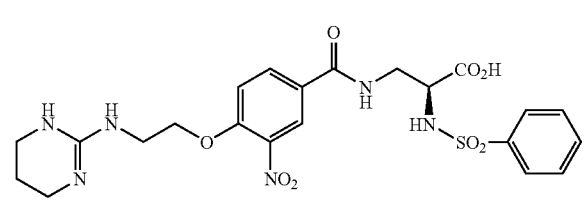
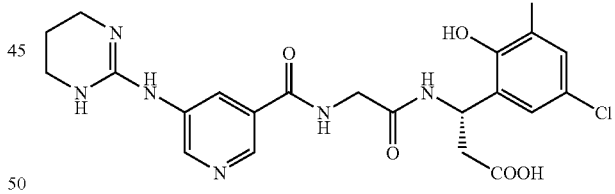
Acylpyridine
and other compounds of document WO 99/52896
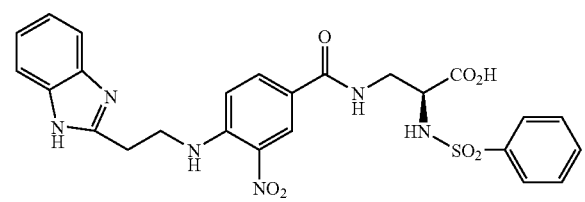
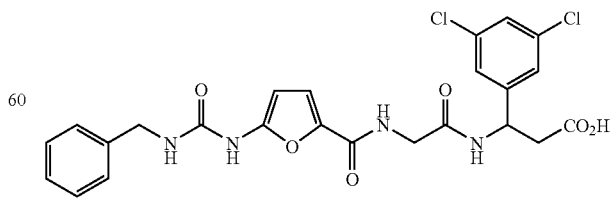
Heteropentacycle core and other compounds from the document Lohof et al., Angew. Chem. Int. Ed. Eng 2000, 39(15), pp. 2761-2764

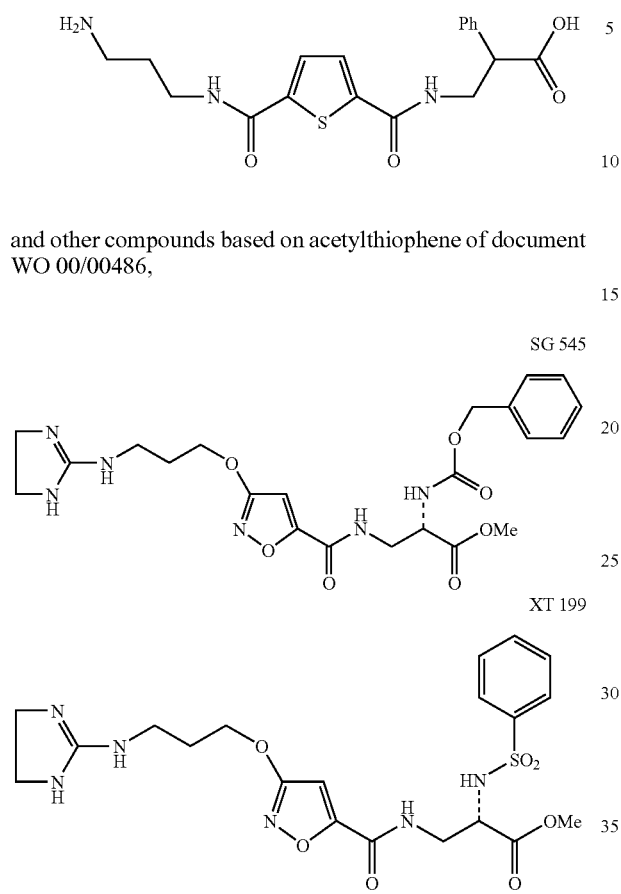

and other compounds based on acetylthiophene of document WO 00/00486, (and the compounds SG256, SM256 and XJ735 from Dupont Pharmaceuticals)

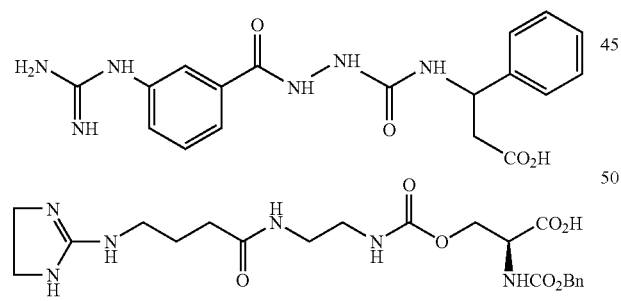

and analogs from the document WO 00/03973

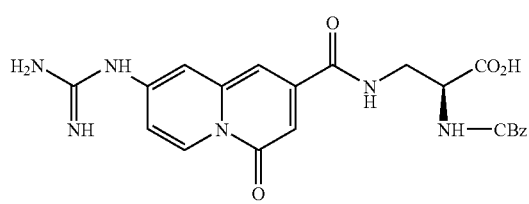

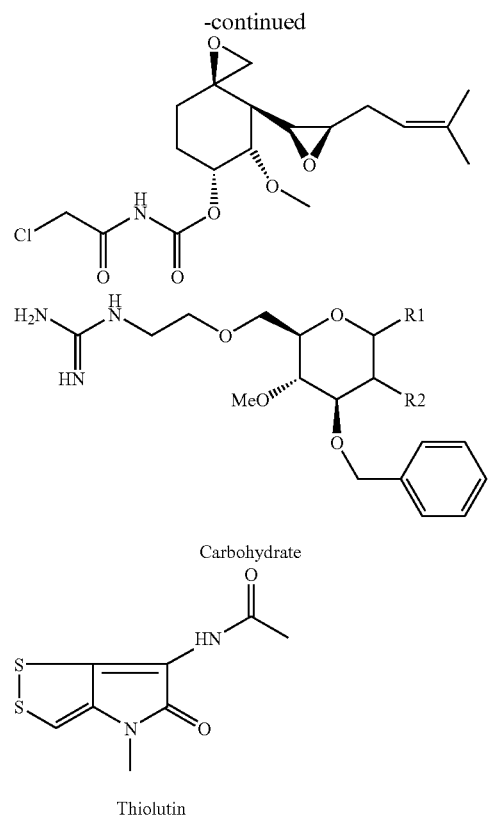

Thiolutin and other compounds with a pyrrothine group.

Use may also be made of biovectors mentioned in documents U.S. Pat. No. 6,537,520 (biovectors targeting αvβ3 overexpressed during angiogenesis) and WO 01/198294 (indazole core). In certain cases, use may be made of several different biovectors in the same compound in order to increase the chances of attaining the same target, for example an RGD peptide and a benzodiazepine for αvβ3. In addition to the biovectors of the RGD type or functional equivalents mentioned above, use may be made of the following MMP-inhibiting compounds, in the knowledge that the detailed description gives experimental protocols which make it possible to finalize an in vitro or in vivo screening:

- peptides, peptidomimetics, functionally equivalent non-peptides, which are effective in diagnostic or therapeutic terms, selected from commercially available inhibitors, in particular in the 2002 catalogs of Bachem, Amersham;
- inhibitors described in documents WO 01/60416, WO 01/60820, WO 2001/92244, EP 558 635, EP 663 823;
- inhibitors of the type such as hydroxamates, pyrrolidine hydroxamates, bicyclic hydroxamates, cyclobutyl hydroxamates, succinyl hydroxamates, sulfonamide hydroxamates, alanine hydroxamates, as described in documents EP 793 641, EP 766 665, EP 740 655, EP 689 538, EP 575 844, EP 634 998, WO 99/29667, EP 965 592, EP 922 702, WO 99/52889, WO 99/42443, WO 01/60416 (Dupont; in particular of formulae Ia and Ib);
- phosphinic acid-based inhibitors as described in documents EP 725 075, U.S. Pat. No. 5,679,700, WO 98/03516, EP 716 086, WO 2000 74681, WO 2000 04030;
- cyclic imide-based inhibitors (U.S. Pat. No. 5,854,275);

tricyclic sulfonamide-based inhibitors (WO 2000 06561); oxobutyric acid-based inhibitors;

derivatives of TIMPS (*Bioconjugate Chem*, 2001, 12, 964-971).

Still in the oncology field, compounds (III) in which the biovector is based on phosphonates or on bisphosphonates are very useful for cancer of bone tissues. These compounds are also useful for diseases related to bone problems, due to problems of immunity (autoimmune diseases such as rheumatoid arthritis), to metabolic diseases (osteoporosis etc.) infectious diseases.

In these compounds, the biovector is, for example, a biovector described in document WO 02/062398. Use may also be made of a bisphosphonate described in U.S. Pat. No. 6,534,488 or U.S. Pat. No. 6,509,324, a commercially available bisphosphonate such as etidronate, clodronate, pamidronate, alendronate, ibandonate, YH 592 or EB-1053, and the like.

C) Field of Inflammatory and Degenerative Diseases

Biovectors which are ligands for receptors located on macrophages, such as SRA receptors (scavenger receptors) or Fc receptors (US 2002/58284), will in particular be targeted.

The progression of atherosclerosis involves the capture of LDLs and then the oxidation thereof in plaques. The phagocytosis of these oxidized LDLs by macrophages is mediated by a set of receptors referred to as scavenger receptors (SRs). This family of membrane-bound proteins therefore plays a major role in the gradual conversion of macrophages to foam cells. SRs are membrane-bound surface proteins capable of binding senescent cells and also chemically or biologically modified lipoproteins. The main SR groups are classified into various classes:

1/ class A SRs: type I, type II and MARCO
2/ class B SRs: type I, type II and CD36
3/ class D SRs: CD68
4/ class E and F SRs, "lectin-like": LOX-1
5/ recent unclassified SRs: SR-PSOX.

As recalled in document US A 2002/0127181 and in De Winther et al., *ATVB* 2000; 20: 290-297; Kunjathoor et al., *J. Biol. Chem.* 2002; 277: 49982-49988, the SRA receptor is overexpressed by macrophages in cardiovascular diseases (atherosclerosis, atheroma plaque, coronary artery disease, thrombosis, ischemia, myocardial infarction etc.). The use of products according to the invention for targeting SRA associated with these pathologies is part of the invention.

The invention thus also covers, for the diagnosis and/or treatment of inflammatory diseases, particles complexed by compounds of formula (I) associated:

1) with SR-targeting biovectors, in particular:

1a) biovectors described in documents U.S. Pat. No. 6,255,298, U.S. Pat. No. 6,458,845, WO 00/06147, WO 00/03704;

1b) modified lipoproteins, in particular acetylated LDLs (acLDL; Gurudutta et al., Nucl. Med. Biol. 2001 28: 235-24) and oxidized LDLs (oxLDL);

1c) AcLDL, OxLDL and LPS ligands described in Esbach et al., *Hepatology*, 1993 18: 537; De Rijke et al., *J. Biol. Chem*, 1994, 269: 824; Van Oosten et al., *Infect. Immun.* 1998, 66: 5107; Bijsterbosch et al., *Nucleic Acids Res.* 1997 25: 3290; Biessen et al, *Mol. Pharmacol.* 53: 262, 1998;

1d) peptides screened by phage display, capable of binding to the SR-AI receptor;

2) with folate receptor-targeting biovectors (these folate receptors are overexpressed in activated macrophages) for use in pathologies involving macrophage activation;

3) with peptides for targeting amyloid plaques leading in particular to Alzheimer's disease (for example, described in WO 01/74374, U.S. Pat. No. 6,329,531);

4) with biovectors of the CSF type (GCSF, GM-CSF, etc.) described, for example, in U.S. Pat. No. 6,491,893;

5) with antibodies or antibody fragments which target receptors overexpressed on macrophages (CD68, MRP8-14, etc.).

In the field of inflammatory diseases, the inventors have in particular used phosphatidylserine or a derivative of phosphatidylserine as a biovector for use in the diagnosis of macrophage-related diseases.

Phosphatidylserine (PS) is a membrane phospholipid located mainly on the inner face of the cell on the cytoplasmic side. Its overall negative charge stabilizes its polarity and prevents it from diffusing across the plasma membrane. PS serves as a recognition signal for the macrophage. The nature of this signal is still unknown (direct recognition, charge density, multiple receptors, inducible single receptor). According to the latest studies published, it is thought to be a direct interaction between PS and PS receptor (PSR) after induction of this receptor at the surface of certain macrophages present in the region undergoing a rupture of homeostasis. In some macrophage cells, PS also interacts with the scavenger receptors via their site of attachment for anionic phospholipids. PS is expressed on the inner face of the membrane of all viable cells. In the event of cell suffering, or at the beginning of the apoptotic process, a membrane-bound translocase causes the PS to flip onto the extracellular face of the cell. This extracellular expression constitutes a recognition signal for macrophages, which recognize and phagocytose the suffering cell, thus avoiding a local inflammation.

The inventors have prepared a contrast agent bonded to PS or derivative, intended to be actively taken up by macrophages in order to image these various pathologies. Several chemical technical difficulties have been overcome in order to prepare the following PS biovectors, the chelate being coupled to the free $NH_2$ group:

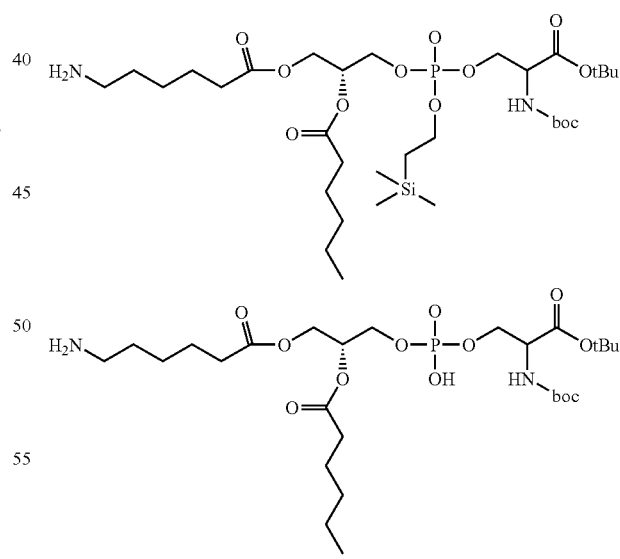

In order to completely control the structure of the final products, it has been necessary to prepare correctly functionalized PS derivatives. The presence of an amino acid residue on the polar portion of the PS is a source of further difficulties which had to be controlled by performing chemistry to protect/deprotect the free amine and acid groups, and/or by using chemical methods compatible with these groups. The groups which protect the amino acid residue are the conventional groups used in amino acid chemistry (Boc, tBu, Z, Bn, etc.). The groups preferred to provide the bond between the PS and the superparamagnetic particle are $NH_2$, COOH and SH.

The inventors have also prepared vectorized products in which the phosphatidylserine lacks at least one of the fatty chains, the affinity not being altered in an interfering manner.

In addition to those already mentioned above in the present application in the fields, use may also be made of:

1) The biovectors described in documents WO 01/97850 (targeting VEGF receptors and angiopoietin), U.S. Pat. No. 6,372,194 (polymer such as polyhystidine), WO 2001/9188 (fibrin-targeting polypeptide), WO 01/77145 (integrin-targeting peptide), WO 02/26776 (αvβ3 integrin-targeting peptide), WO 03/062198 (MMP metalloprotease-targeting peptides), WO 99/40947 (peptides targeting, for example, the KDR/Flk-1 receptor, including R-X-K-X-H and R-X-K-X-H, or the Tie-1 and 2 receptors), WO 02/062810 and Müller et al, Eur. J. Org. Chem, 2002, 3966-3973 (sialyl Lewis glycosides), WO 02/40060 (antioxidants such as ascorbic acid), U.S. Pat. No. 6,524,554 (targeting of tuftsin), WO 02/094873 (targeting of G-proteinreceptors GPCRs, in particular cholecystokinin), U.S. Pat. No. 6,489,333 (integrin antagonist and guanidine mimetic combination), U.S. Pat. No. 6,511,648 (quinolone targeting αvβ3 or αvβ5), US A 2002/0106325, WO 01/97861 (benzodiazepines and analogs targeting integrins), biovector for targeting integrin, including α5β1, WO 01/98294 (imidazoles and analogs), WO 01/60416 (MMP inhibitors, in particular hydroxamates), WO 02/081497 (αvβ3-targeting peptides such as RGDWXE), WO 01/10450 (RGD peptides), U.S. Pat. No. 6,261,535 (antibodies or antibody fragments (FGF, TGFb, GV39, GV97, ELAM, VCAM, inducible with TNF or IL)), U.S. Pat. No. 5,707,605 (targeting molecule modified by interaction with its target), WO 02/28441 (amyloid-deposit targeting agents), WO 02/056670 (cathepsin-cleaved peptides), U.S. Pat. No. 6,410,695 (mitoxantrone or quinone), U.S. Pat. No. 6,391,280 (epithelial-targeting polypeptides), U.S. Pat. No. 6,491,893 (GCSF), US 2002/0128553, WO 02/054088, WO 02/32292, WO 02/38546, WO 2003/6059, U.S. Pat. No. 6,534,038, WO 99/54317 (cysteine protease inhibitors), WO 0177102, EP 1 121 377, Pharmacological Reviews (52, no 2, 179; growth factors is PDGF, EGF, FGF, etc.), Topics in Current Chemistry (222, W. Krause, Springer), Bioorganic & Medicinal Chemistry (11, 2003, 1319-1341; αvβ3-targeting tetrahydrobenzazepinon derivatives).

2) Angiogenesis inhibitors, in particular those tested in clinical trials or already commercially available, especially:

antiogenesis inhibitors involving FGFR or VEGFR receptors, such as SU101, SU5416, SU6668, ZD4190, PTK787, ZK225846, azacycle compounds (WO 00/244,156, WO 02/059110);

angiogenesis inhibitors involving MMPs, such as BB25-16 (marimastat), AG3340 (prinomastat), solimastat, BAY12-9566, BMS275291, metastat, neovastat;

angiogenesis involving integrins, such as SM256, SG545, EC-ECM-blocking adhesion molecules (such as EMD 121-974, or vitaxin);

medicinal products with a more indirect mechanism of antiangiogenesis action, such as carboxiamidotriazole, TNP470, squalamine, ZD0101;

the inhibitors described in document WO 99/40947, monoclonal antibodies very selective for binding to the KDR receptor, somatostatin analogs (WO 94/00489), selectin-binding peptides (WO 94/05269), growth factors (VEGF, EGF, PDGF, TNF, MCSF, interleukins); VEGF-targeting biovectors described in Nuclear Medicine Communications, 1999, 20;

the inhibitory peptides of document WO 02/066512.

3) Biovectors capable of targeting receptors: CD36, EPAS-1, ARNT, NHE3, Tie-1, 1/KDR, Flt-1, Tek, neuropilin-1, endoglin, pleiotrophin, endosialin, Axl., alPi, a2ssl, a4P1, a5pl, eph B4 (ephrin), laminin A receptor, neutrophilin 65 receptor, OB-RP leptin receptor, CXCR-4 chemokine receptor (and other receptors mentioned in document WO 99/40947), LHRH, bombesin/GRP, gastrin receptors, VIP, CCK, Tln4.

4) Biovectors of the tyrosine kinase inhibitor type.

5) Known inhibitors of the GPIIb/IIIa inhibitor selected from:

(1) the fab fragment of a monoclonal antibody for the GPIIb/IIIa receptor, Abciximab (ReoPro™),
(2) small peptide and peptidomimetic molecules injected intravenously, such as eptifibatide (Integrilin™) and tirofiban (Aggrastat™).

6) Peptides which are fibrinogen receptor antagonists (EP 425 212), peptides which are IIb/IIIa receptor ligands, fibrinogen ligands, thrombin ligands, peptides capable of targeting atheroma plaque, platelets, fibrin, hirudin-based peptides, guanine-based derivatives which target the IIb/IIIa receptor.

7) Other biovectors or biologically active fragments of biovectors known to the person skilled in the art as medicinal products, with antithrombotic action, anti-platelet aggregation action, action against atherosclerosis, action against restenosis, and/or anticoagulant action.

8) Other biovectors or biologically active fragments of biovectors which target αvβ3, described in combination with DOTA in U.S. Pat. No. 6,537,520, selected from the following: mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustin, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, alpha-interferon, alpha2-interferon, beta-interferon, gamma-interferon, colony stimulating factor-1, colony stimulating factor-2, denileukin diftitox, interleukin-2, leutinizing hormone releasing factor.

9) Some biovectors which target specific types of cancer, for example peptides which target the ST receptor associated with colorectal cancer, or the tachykinin receptor.

10) Biovectors which use phosphine-type compounds.

11) Biovectors for targeting P-selectin, E-selectin; for example the 8-amino acid peptide described by Morikawa et al, 1996, 951, and also various sugars.

12) Annexin V or biovectors which target apoptotic processes.

13) Any peptide obtained by screening technologies such as phage display, optionally modified with unnatural amino acids (http//chemlibrary.bri.nrc.ca), for example peptides derived from phage display libraries: RGD, NGR, CRRETAWAC, KGD, RGD4C, XXXY*XXX, RPLPP, APPLPPR.

14) Other known peptide biovectors for targeting atheroma plaques, mentioned in particular in document WO 2003/014145.

15) Vitamins.

16) Ligands for hormone receptors, including hormones and steroids.

17) Opioid receptor-targeting biovectors.

18) TKI receptor-targeting biovectors.

19) LB4 and VnR antagonists.

20) Nitriimidazole and benzylguanidine compounds.

21) Biovectors recalled in Topics in *Current Chemistry*, vol. 222, 260-274, Fundamentals of Receptor-based Diagnostic Metallopharmaceuticals, in particular:

biovectors for targeting peptide receptors overexpressed in tumors (LHRH receptors, bombesin/GRP, VIP receptors, CCK receptors, tachykinin receptors, for example), in particular somatostatin analogs or bombesin analogs, optionally glycosylated octreotide-derived peptides, VIP peptides, alpha-MSHs, CCK-B peptides;

peptides selected from: cyclic RGD peptides, fibrin-alpha chain, CSVTCR, tuftsin, fMLF, YIGSR (receptor: laminin).

22) Oligosaccharides, polysaccharides and ose derivatives, Glu-targeting derivatives.

23) Biovectors used for products of the smart type.

24) Markers of myocardial viability (tetrofosmin and hexakis-2-methoxy-2-methylpropyl isonitrile).

25) Sugar and fat metabolism tracers.

26) Ligands for neurotransmitter receptors (D, 5HT, Ach, GABA, NA receptors).

27) Oligonucleotides.

28) Tissue factor.

29) Biovectors described in WO 03/20701, in particular PK11195, a ligand for the peripheral benzodiazepine receptor.

30) Fibrin-binding peptides, in particular the peptide sequences described in WO 03/11115.

31) Amyloid plaque aggregation inhibitors described in WO 02/085903.

32) A biovector of the fluorochrome type which can be used in optical imaging.

Where appropriate, the length of the linker L of the compound (I) will be varied in order to optimize the biodistribution of the compound (III) and/or to promote its specific recognition by the biological target.

Final Particles

In the context of the invention, the final particles, complexed and optionally coupled to the biovector(s), the overall hydrodynamic diameter of which is between 5 nm and 200 nm, preferably between 5 and 60 nm, are preferred.

The compositions of magnetic particles (p), optionally coupled to the biovectors, are generally in the form of an aqueous suspension, optionally in the presence of a water-miscible organic solvent such as DMSO, acetone or methanol, biocompatible suspensions being particularly preferred.

According to a preferred variant of the invention, the compositions of acid magnetic particles (p) complexed and optionally coupled to biovectors comprise one or more pharmaceutically acceptable vehicle(s) and/or additive(s). In this context, sterile compositions are particularly preferred.

Process for Preparing the Particles

According to another aspect, a subject of the invention is a process for the preparation of acid magnetic particles (p) in which at least 90% of the protonated sites are complexed by one or more identical or different gem-bisphosphonate compounds of formula (I), it being possible for the X groups to be coupled to at least one biovector, said process comprising bringing an acid solution of acid magnetic particles (p) based on an iron compound into contact with compounds of formula (I) as defined above in sufficient amount, and recovering the complexed particles obtained.

According to another aspect, a subject of the invention is a process for the preparation of a composition of magnetic nanoparticles complexed by compounds (I) and covered with biovectors, comprising the successive steps consisting in:

i) bringing an acid solution of acid magnetic particles (p) based on an iron compound into contact with compounds of formula (I) as defined above in sufficient amount, and recovering the complexed particles obtained;

ii) coupling all or some of the X groups of the compounds of formula (I) complexed at the surface of the magnetic particles (p) with biovectors.

Preferably, step i) comprises the following steps i1) and i2):

i1) preparing an acid solution of acid magnetic particles (p) based on an iron compound;

i.2) bringing the solution from i.1) into contact with compounds of formula (I) as defined above in sufficient amount, and recovering the complexed particles obtained.

According to a preferred embodiment of the process according to the invention, the acid ferrofluid used in step i) comprises magnetic particles based on ferrite, preferably on maghemite or on magnetite.

Generally, step i) is carried out in aqueous medium, optionally in the presence of a water-miscible solvent, such as DMSO, acetone or methanol, at an acid pH, preferably a pH of 1 to 3.

Without wishing to be limited to any theory, during the step consisting of the complexing of magnetic particles (p), the initially protonated sites of the magnetic particles (p) interact with the gem-bisphosphonate end of the compounds of formula (I) via the expulsion of protons as described in particular in the publication by N. Fauconnier et al.: *Prog. Colloid Polym. Sci.* (1996), 100, pp. 212-216. The protonated sites of the acid magnetic particles (p) can therefore be considered as "points of attachment or points of bonding" of the gem-bisphosphonate groups of the compounds of formula (I) to the surface of the magnetic particle.

According to a particularly preferred embodiment, the procedure is carried out in the presence of an amount ranging from 1 to 3 molar equivalents relative to the number of moles of hydroxyl sites protonated at the surface of the particle (p), so as to complex at least 70%, and preferably more than 90%, of the protonated sites of the magnetic particle (p). This represents, in general, approximately 40 to 200 compounds of formula (I) per particle, depending on the size thereof, the number of surface protonated sites being proportional to the surface of the acid magnetic particle (p).

Advantageously, the evaluation of the degree of grafting which defines the ratio of the number of moles of compounds of formula (I) to the number of moles of protonated sites of the acid magnetic particle (p) can be readily determined by conventional methods such as C, P and Fe elemental analysis. Specifically, the acid magnetic particle (p), before grafting of the compound (I), comprises no phosphorus atom or carbon atom. Now, after grafting of the compounds (I) to the surface of the particle, determination of the phosphorus/iron ratio makes it possible to determine the number of moles of compound (I) grafted onto the acid magnetic particle (p).

Moreover, the number of protonated sites per magnetic particle is accessible according to conventional techniques known to the person skilled in the art, such as conductimetry or acid-based assays.

By virtue of these analytical tools, it is possible to adjust the amount of compound of formula (I) according to the degree of grafting that it is desired to ultimately obtain.

Advantageously, this process therefore makes it possible to control the grafting of the magnetic particle (p) with the compounds of formula (I).

Against all expectations, particularly advantageously compared to the prior art which did not use acid particles, the inventors have also shown that, unlike the case of grafting onto alkaline particles, the acid magnetic particle (p) grafted with compounds of formula (I) is most commonly stable within a pH of from 3 to 12, in particular at physiological pH, which constitutes a major advantage for carrying out the subsequent coupling of biovectors, including in particular of proteins or antibodies, without degrading them or denaturing them.

This property was not evident given that, in general, the grafting of a complexing agent, whatever it is, to the surface of a particle modifies the surface charge of the particles and therefore their stability range as a function of pH and the ionic strength.

Unexpectedly, the inventors have also observed very good selectivity between the gem-bisphosphonate group and the reactive X group: only the gem-bisphosphonate groups are complexed at the surface of the magnetic particle.

Advantageously, unlike the prior art, isolation of the complexed magnetic particles does not require any laborious purification steps, for example using dialysis or treatment on a resin.

After complexation, the acid magnetic particles (p) complexed by the compounds of formula (I) form a flocculate which can be, according to a preferred embodiment, isolated from the reaction medium by simple magnetic separating.

Prior to step (ii), the recovered flocculate is washed several times with water so as to remove the excess compounds of formula (I) which have not reacted.

At the end of step (i), the recovered flocculate is generally suspended in an aqueous solution having a pH of between 6 and 7, which results in disaggregation of the flocculate (peptization) and the production of a colloidal solution.

According to a preferred embodiment, a prior step is carried out consisting in suspending the flocculate formed in step (i) in an aqueous solution having a basic pH of between 10 and 11, before returning to a pH of between 6 and 7. This treatment at basic pH is in fact aimed at reinforcing the bonding of the gem-bisphosphonate compound to the surface of the acid magnetic particle (p).

According to an advantageous aspect, the acid magnetic particles (p) complexed by the gem-bisphosphonate compounds, obtained at the end of step (i), are relatively non-polydispersed and exhibit a "hydrodynamic size" profile very similar to the starting acid ferrofluid. This complexing step does not therefore produce any phenomenon of aggregation, which makes it possible to avoid any addition filtration step.

According to another advantageous aspect, the magnetic particles complexed by the gem-bisphosphonate compounds are obtained with very good iron yields, generally between 70 to 95%.

The acid magnetic particles (p) grafted with compounds of formula (I) are advantageously stable at physiological pH in the presence, optionally, of a solvent, which makes it possible to carry out the coupling of the biovectors directly in ferrofluid medium.

The prior art did not in any way suggest grafting gem-bisphosphonate compounds onto acid particles.

According to another advantageous aspect, the reactive X group of the compound of formula (I) grafted to the surface of the particle has very good reactivity with respect to the biovectors, and makes it possible to obtain high coupling yields. This therefore makes it possible to decrease the losses of biovectors used and to thus decrease the cost of the specific magnetic particle ultimately obtained.

Another particularly advantageous aspect is the determination of the degree of coupling of the biovector to the magnetic particle (p) grafted with compounds of formula (I). In fact, the composition, determined by elemental analysis (C, P, Fe), of the magnetic particle (p) grafted with compounds of formula (I) makes it possible to exactly determine the phosphorus/iron ratio, and the elemental analysis of the final particles onto which a biovector is grafted makes it possible in the same way to determine the nitrogen/phosphorus or carbon/phosphorus ratio, which makes it possible to calculate the number of biovectors on each particle. This type of analysis is completely impossible on the magnetic particles obtained by "Molday" synthesis, coated with polymers such as dextran to which specific affinity molecules have been grated, due to the polydispersed nature of the coating polymer.

Step (ii) consists in bringing the magnetic particles (p) complexed by gem-bisphosphonate compounds into contact with a sufficient amount of biovector, generally in ferrofluid medium, with stirring at ambient temperature for a few hours, the amount of biovector used being fixed as a function of the degree of coupling that it is desired to obtain.

At the end of step ii), a filtration step can be carried out in order to separate the magnetic particles (p), coupled with biovectors, from the possible biovectors which have not reacted.

According to a preferred variant, the acid magnetic particles (p) used in step (i) are obtained according to a process comprising the steps consisting in:

a) preparing a colloidal solution of acid ferrofluid;

b) treating the solution obtained in step a) with a nitric acid solution;

c) isolating the acid flocculate obtained in step b);

d) carrying out a peptization.

Steps a) to c) correspond, in this variant, to steps i.1) and i.2) described above.

The preparation of the colloidal solution of acid ferrofluid carried out in step a) is well known and described in many references. Mention may in particular be made to patent FR 7918842 and to the publications *C. R. Acad. Sc. Paris* (Jul. 7, 1980), t. 291—series C and *IEE Transactions on Magnetics*, 1981, vol. MAG-17, no 2, p. 1247.

By way of indication, "acid" and "alkaline" ferrofluids are generally obtained by bringing an aqueous solution containing $Fe^{2+}$ and $Fe^{3+}$ salts in suitable proportions into contact with a basic solution, in general aqueous ammonia.

The peptization or disaggregation of the gelatinous precipitate obtained with an acid solution, generally of perchloric or nitric acid, results in an "acid" ferrofluid being obtained, whereas peptization with a solution of tetramethylammonium hydroxide (TMAOH) leads to "alkaline" ferrofluids being obtained.

"Alkaline" ferrofluids are not suitable for the invention in that the process for obtaining them is such that their hydrodynamic size cannot be readily controlled, and that, after grafting of the compounds of formula (I), they require long and laborious purification steps such as dialysis or filtration on resins. In addition, since TMAOH is toxic, the biomedical application of the resulting alkaline ferrofluids means that further treatments aimed at removing all traces of TMAOH must be carried out.

On the other hand, it is possible to envision, in the context of the present invention, the use of "acid" ferrofluids resulting from the conversion of "alkaline" ferrofluids according to processes described in the literature, in particular in the following publications: R. Massart, V. Cabuil (*Journal de*

*Chimie-Physique* [Journal of Chemistry-Physics], 1987, 84, no 7-8, p. 967-973); R. Massart, CR Acad. Sc. Paris, t. 291 (Jul. 7, 1980), series C1.

According to a preferred embodiment of the process according to the invention, the acid ferrofluid used in step a) comprises magnetic particles based on ferrite, preferably on maghemite or on magnetite.

In this context, the acid ferrofluids based on ferrite resulting from further treatment with a solution of $Fe(NO_3)_3$ are particularly preferred. This further treatment, carried out at the end of step a), makes it possible to carry out a core oxidation of the magnetic particles (p) based on ferrite, and advantageously to decrease the phenomena of cellular toxicity associated with the presence of $Fe^{2+}$ ions. In addition, this treatment makes it possible to increase the stability of the final ferrofluid solution obtained at the end of step d).

Advantageously, the treatment used in step b) makes it possible to control the hydrodynamic size of the magnetic particles obtained in step a).

Thus, the inventors have discovered, unexpectedly, that the size of the magnetic particles obtained in step a) can be decreased provided that the concentrations and duration of treatment with nitric acid are adjusted.

Preferably, use is made in step b) of a nitric acid solution having a concentration of between 1.5 and 4 mol/L. In particular, in this case, the treatment is applied for a period ranging generally from 1 hour to 48 hours, and preferably for a period at least equal to 2 H, and preferably less than 24 H.

At the end of this treatment, the flocculate obtained is isolated in step c) advantageously by simple magnetic separation and washed several times with an organic solvent such as acetone.

Finally, the flocculate isolated in step c) is suspended in a volume of aqueous solvent, optionally in the presence of a water-miscible organic solvent allowing peptization, that is to say disaggregation of the flocculate and the production of a colloidal solution of acid ferrofluid.

The invention is also aimed at the compositions, as such, comprising acid magnetic particles (p) complexed by compounds of formula (I) and coupled to biovectors, which can be obtained by the process comprising steps (i) and (ii).

According to another aspect, a subject of the invention is a composition, as such, comprising the acid magnetic particles (p) complexed by compounds of formula (I), which can be obtained in step (i) of the process according to the invention.

Also included in the invention are the compositions comprising a mixture of these magnetic particles with the magnetic particles coupled to biovectors.

Applications

The invention also relates to contrast products for medical magnetic resonance imaging, which comprise the compositions of acid magnetic particles (p) optionally coupled to biovectors, optionally combined with a pharmaceutically acceptable vehicle and with pharmaceutically acceptable additives.

When the particle is not coupled to a biovector, the X group of the gem-bisphosphonate compound is selected such that it does not induce a toxic reaction in vivo. In this context, it is particularly preferred for X to represent —COOH or —$NH_2$. In the absence of coupling to a biovector, the compositions of magnetic particles (p) complexed with the compounds of formula (I) may, by way of example, be used as a contrast agent for angiography by MRI, and also for other MRI applications.

The compositions of magnetic particles (p) complexed with compounds of formula (I) coupled to biovectors are particularly useful for specific magnetic resonance imaging (MRI), in particular the specific magnetic resonance imaging of an organ or of a pathology.

In the absence of coupling to a biovector, the compositions of magnetic particles (p) complexed with the compounds of formula (I) may, by way of example, be used as a contrast agent for angiography by MRI, and also for other nonspecific MRI applications.

The relaxivities $r_1$ and $r_2$ of a magnetic contrast product give a measure of its magnetic efficiency and make it possible to assess its influence on the signal recorded.

In this context, the inventors have shown that the compositions of magnetic particles (p) complexed by the gem-bisphosphonate compounds exhibit very advantageous relaxivities $r_1$ and $r_2$, making it possible to obtain a large increase in the proton relaxation rates ($R_1=1/T1$ and $R_2=1/T2$). This effect on the relaxation rates then makes it possible to obtain a very good contrast in MRI, in the targeted areas.

When the magnetic particles are coupled to biovectors, in particular to ligands specific for a given target biological receptor, the compositions of the invention may be used as contrast agents for specific imaging by MRI, in particular for characterization and therapeutic monitoring in many pathologies: by way of indication, mention may be made of cardiovascular diseases (atheroma plaque imaging), cancers (tumors, metastases), inflammatory and degenerative diseases (multiple sclerosis, rheumatoid arthritis, Alzheimer's disease).

Thus, according to another aspect, a subject of the invention is a method of diagnosis or of therapeutic monitoring in which a composition comprising acid magnetic particles (p) optionally coupled to at least one biovector is administered to a patient, which makes it possible to visualize an organ or a pathology in the patient by magnetic resonance.

By way of example, the final particle compositions for which the biovector used is a folic acid derivative, a metalloprotease inhibitor or an antibody, for example the anti-CEA or anti-mucin type, may be particularly useful as an MRI contrast agent in oncology for the detection and characterization of tumors and for obtaining an overall picture of cancer extention (metastases).

Similarly, the compositions of final particles to which are coupled biovectors such as phosphatidylserine derivatives make it possible to target inflammatory and degenerative diseases, atheroma plaques or stress.

Similarly, the compositions of final particles to which are coupled biovectors such as peptides containing the RGD (arginine-glycine-aspartic acid) sequence make it possible to target integrins expressed during angiogenesis and in thrombotic and inflammatory phenomena. They may therefore be used to monitor, by MRI, the effectiveness of anti-angiogenic treatment in cancerology or anti-thrombotic treatment in cardiology.

In general, the use of biovectors such as monoclonal antibodies or fragments thereof (Fab, $Fab'_2$, sFv) make it possible to achieve high specificity in vivo for targeting pathological areas where the receptors corresponding to the antibodies used are overexpressed.

Advantageously, it has been shown that the relaxivities of the particles (p) complexed by compounds of formula (I) and coupled with a biovector are not altered in comparison with the relaxivities of the intermediate without biovector. In addition, it has been shown that the effectiveness of these compositions does not depend on the nature of the biovector coupled to the particles (p) complexed by compounds of formula (I).

The compositions of magnetic particles which may or may not be coupled to biovectors are also useful for nuclear medicine, using a radioactive iron isotope during synthesis.

According to another aspect, the compositions of acid magnetic particles (p) coupled to biovectors according to the invention can be used for delivering a medicinal product by magnetic targeting. In this context, the magnetic particles (p) are coupled to biovectors having pharmacological and/or cytotoxic properties which can be optionally released under the action of a radiofrequency field in the targeted area.

A subject of the invention is thus a method of therapeutic treatment in which a composition comprising acid magnetic particles (p) coupled to at least one biovector, in combination with a pharmaceutically acceptable vehicle, is administered to a patient requiring such a treatment.

The compositions of acid magnetic particles (p) coupled to biovectors according to the invention are also useful for the treatment by hyperthermia of pathological regions. In this context, a biovector is generally chosen which has a particular affinity for a receptor present in the targeted area, and a radiofrequency field, preferably an outside alternating radiofrequency field, is applied opposite said targeted area.

The compositions of magnetic particles (p) coupled- to biovectors according to the invention are also useful for cell labeling, and in particular the labeling of stem cells, which can be carried out in vitro or ex vivo.

Thus, according to another aspect, the subject of the invention is a method for the in vitro detection and/or separation of cells, comprising:
i) bringing cells into contact with a composition comprising acid magnetic particles (p) coupled to at least one biovector capable of labeling the cells; and
ii) detecting and/or separating the labeled cells obtained.

Preferably, the biovector is a ligand specific for a biological receptor expressed by the cells to be labeled.

In this context a biovector capable of binding specifically to a stem cell receptor is coupled to the magnetic particles (p). The stem cells thus labeled, administered to a patient, then make it possible to follow, under the application of a magnetic field, the movement, location and survival of the exogenous cells by MRI visualization. This application is particularly useful for detecting pathologies related to cell dysfunction.

A subject of the invention is thus a method for the diagnosis of pathologies related to cell dysfunction, comprising:
i) labeling stem cells from a patient according to the above-mentioned method, ex vivo;
ii) administering the labeled stem cells to said patient;
which makes it possible, under the application of a magnetic field, to follow the movement, location and survival of the exogenous cells by MRI visualization and thus to detect pathologies related to cell dysfunction.

Finally, the compositions of magnetic particles (p) coupled to biovectors are particularly useful for magnetic cell sorting, carried out in vitro. In this case, the biovector is generally a ligand selected so as to differentiate and/or separate the compounds bearing a receptor for said biovector from those which do not bear said receptor. By way of example, the biovector may represent a specific annexin, a ligand capable of binding to phosphatidylserine (PS) or phosphatidylethanolamine (PE) in the presence of $Ca^{2+}$. In this case, the use according to the invention makes it possible to differentiate and/or separate the cells exhibiting an abnormal state, that is to say capable of binding to the magnetic particles (p) coupled to annexin biovectors, from the normal cells incapable of binding these particles.

The terms "pharmaceutically acceptable" refer to a composition or a molecular entity which does not produce any allergic reaction, side effects or adverse effects when it is administered to an animal or to a human in an appropriate manner.

The expression "pharmaceutically acceptable vehicles" can denote, in the context of the present description, a solvent, a dispersion medium, antibacterial agents and antifungal agents. The use of such media and agents falls within the competence of the person skilled in the art.

Unless the conventional media or agents are incompatible with the magnetic particles (p) complexed by compounds of formula (I), and coupled to biovectors, their use in the diagnostic compositions can be envisioned. Additional active ingredients can also be incorporated into the compositions according to the invention.

It is understood that, in the methods of treatment of the invention, the compositions are administered in a therapeutically effective amount, which can be adjusted by the person skilled in the art depending on the pathology targeted, the condition of the patient, his or her weight, his or her age, etc.

The compositions of the invention are preferably administered parenterally, or orally, other routes of administration not, however, being excluded, such as, for example, administration rectally, administration in the form of an intravenous injection being particularly preferred.

When oral administration is envisioned, the compositions of the invention are in the form of gelatin capsules, effervescent tablets, bare tablets or coated tablets, sachets, sugar-coated tablets, oral ampoules or solutes, microgranules or forms with prolonged or controlled release.

When parenteral administration is envisioned, the compositions of the invention are in the form of lyophilizates ready to be reconstituted or of injectable solutes and suspensions packaged in ampoules or bottles or prefilled syringes, for slow venous infusion or intravenous injection as a bolus.

The forms for oral administration are prepared by mixing the magnetic particles (p) optionally coupled to biovectors, in particular to an active substance, with various types of excipients or of vehicles such as fillers, disintegrating agents, binders, dyes, flavor enhancers, and the like, and then formulating the mixture in a gelatin capsule, in particular a controlled-release gelatin capsules.

The aqueous solubility and the low osmolality of the particles of the invention make it possible to prepare isotonic aqueous solutions of high concentration and acceptable viscosity for injection.

The forms for parenteral administration are obtained in the conventional manner by mixing the magnetic particles (p) optionally coupled to biovectors with buffers, stabilizers, preserving agents, solubilizing agents, isotonic agents and suspending agents. In accordance with known techniques, these mixtures are then sterilized and then packaged in the form of intravenous injections or of lyophilizates ready to be reconstituted in a sterile pharmaceutically acceptable vehicle.

The solutions can be prepared extemporaneously from the lyophilized powder containing the magnetic particles (p) optionally coupled to the biovectors and, optionally, additives and a sterile solvent, or, due to the great stability of the magnetic particles coupled to the biovectors in solution, the solutions can be provided to the radiologist in bottles, ampoules, syringes or bags.

For the preparation of suppositories, the magnetic particles according to the invention are mixed, in a manner known in itself, with a suitable basic constituent such as polyethylene glycol or hemisynthetic glycerides.

The unit doses will depend on the composition of the magnetic particles (p) coupled to biovectors, on the route of administration, on the type of diagnosis to be established, and also on the patient. The unit doses will in general be from 0.01 µmol to 100 µmol of magnetic particles for an individual of average size (75 kg).

As demonstrated in the examples, the inventors have succeeded in obtaining compounds which are both stable and specific, using, as covering, gem-bisphosphonate compounds. It is specified that, more broadly, the applicant is studying coverings capable of binding, firstly, to magnetic particles and, secondly, to at least one biovector. Various coverings are studied, of formula Y1-Y2-Y3, Y1 being at least one group capable of coupling to nanoparticles, Y3 being at least one group capable of interacting with at least one biovector, Y2, which may be present or absent, being a linker between Y1 and Y3. Among Y1s, phosphonates, phosphates, bisphosphonates and analogs other than gem-bisphosphonates, hydroxamates or gem-hydroxamates are in particular studied.

In the remaining text, examples of preparation of compositions according to the invention are described by way of illustration.

In the examples below, the following generalities are specified.

In the following, the abbreviations M, M/L, theoretical M, N and M/z, ES+, ES−, kD and TLC have the following meanings:

M or M/L: molar concentration (mol/liter).
theoretical M: theoretical molecular mass.
N: normality.
M/z: mass charge determined by mass spectrometry.
ES+: positive-mode electrospray.
ES−: negative-mode electrospray.
TFA: trifluoroacetic acid
kD: unit of molecular mass (kiloDalton)
TLC: thin layer chromatography
Z ave: hydrodynamic diameter measured by PCS
Poly σ: polydispersity measured by PCS.

The chemical nomenclature which follows is derived from the ACD/NAME software (Advanced Chemistry Development Inc, Toronto, Canada), according to IUPAC rules.

Total Iron Assay:

The iron is assayed by atomic absorption spectroscopy (VARIAN AA10 spectrophotometer) after mineralization with concentrated HCl and dilution with respect to a standard range of ferric ions (0, 5, 10, 15 and 20 ppm).

Particle Size:

Hydrodynamic Diameter of the Grafted Particle (Z ave)= PCS Size:

Determined by PCS (Malvern 4700 device, laser 488 nm at 90°) on a sample diluted to ~1 millimolar with water for injectable preparation, filtered through 0.22 µm.

PCS=Photon Correlation Spectroscopy—Reference: R. Pecora in *J. of Nano. Res.* (2000), 2, p. 123-131.

Diameter of the Magnetic Particles (p) (Before Grafting)

Determined by deconvolution of magnetization curves (measurements taken on a SQUID magnetometer) at various temperatures. [Reference: R. W. Chantrell in *IEEE Transactions on Magnetics* (1978), 14(5), p. 975-977.

Determination of the Degree of Grafting by Microanalysis:

Compound A: expressed in moles per hundred moles of total iron.

Other compounds: expressed in moles per hundred moles of iron and in moles per hundred moles of compound A.

Structural Analyses:

By mass spectroscopy (MICROMASS VG Quattro II device) with an Electrospray source.

Relaxivity Measurements:

The relaxation times T1 and T2 were determined by standard procedures on a Minispec 120 device (Bruker) at 20 Mhz (0.47 T) and 37° C. The longitudinal relaxation time T1 is measured using an inversion recuperation sequence and the transverse relaxation time T2 is measured by a CPMG technique.

The relaxation rates R1 (=1/T1) and R2 (=1/T2) were calculated for various concentrations of total metal (ranging from $0.1 \times 10^{-3}$ to $1 \times 10^{-3}$ mol/L) in aqueous solution at 37° C. The correlation between R1 or R2 as a function of concentration is linear, and the slope represents the relaxivity r1 (R1/C) or r2 (R2/C) expressed as (1/second)×(1/mmol/L), i.e. $(mM^{-1} \cdot s^{-1})$.

EXAMPLE OF COMPOUNDS OF FORMULA (I)

Example 1

Preparation of Compound A

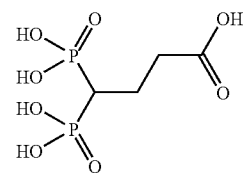

1) Diethyl-1-[ethoxyphosphoryl]vinyl phosphonate 13 g (0.433 mol) of paraformaldehyde and 10 ml (0.097 mol) of diethylamine are solubilized under hot conditions in 250 ml of methanol. 24 g ($8.67 \times 10^{-2}$ mol) of diethyl[ethoxy(propyl)phosphoryl]methyl phosphonate are then added. The mixture is brought to reflux for 24 hours. The reaction medium is concentrated under vacuum. The concentrate is taken up twice with 250 ml of toluene and is then concentrated under vacuum.

The oil obtained is solubilized in 125 ml of toluene. 0.14 g of para-toluenesulfonic acid are added. The mixture is brought to reflux for 24 hours with a Dean-Stark trap and is then concentrated to dryness under vacuum.

The product is extracted with 500 ml of $CH_2Cl_2$ and is then washed twice with 250 ml of water. The organic phase is dried over $MgSO_4$ and concentrated under vacuum.

The crude product is purified on 625 g of Merck Geduran® silica gel (40-63 µm). Elution: $CH_2Cl_2$/acetone-50/50 (TLC-$SiO_2$: Rf=0.45).

18.4 g are isolated with a yield of 71%.

Mass spectrum: M/z=301.4 (ES+) theoretical M=300.2

$C^{13}$ spectrum: (s) 148.8 ppm, (t) 134.8-131.5-128.2 ppm, (s)

62.2 ppm, (s) 16.7 ppm $H^1$ spectrum: (t) 6.9-6.8-6.6 ppm, (unresolved peak) 3.9 ppm, (t) 1.15 ppm.

2) Diethyl 2-[2.2-bis(diethylphosphoryl)ethyl]malonate 1.6 g (0.01 mol) of diethyl malonate, 0.07 g (0.001 mol) of sodium ethoxide and 3 g (0.01 mol) of diethyl[ethoxy(propyl)

phosphoryl]vinyl phosphonate are stirred for 15 min in 15 ml of ethanol. [TLC: $SiO_2$; eluent $CH_2Cl_2$/acetone 50/50-Rf=0.6].

5 ml of a saturated $NH_4Cl$ solution are added to the ethanolic solution. The mixture is concentrated under vacuum. The residue is extracted with 30 ml of ethyl acetate and washed twice with 5 ml of water. The organic phase is dried over $MgSO_4$ and is then evaporated to dryness.

The oil obtained is purified on 200 g of Merck Geduran® silica (40-63 μm). Elution $CH_2Cl_2$/acetone 50/50 Rf=0.6

3.8 g are isolated with a yield of 82%.

Mass spectrum: M/z 460.9 (ES+), theoretical M=460.

3) 4,4-Diphosphonobutanoic acid 7 g ($15.7 \times 10^{-2}$ mol) of diethyl 2-[2.2-bis(diethylphosphoryl)ethyl] malonate are brought to reflux for 8 hours in 350 ml of HCl [5N].

The brown oil obtained is purified on 60 g of silanized silica 60 (0.063-0.200 mm) with water elution [HPLC monitoring].

3.6 g are isolated with a yield of 92%.

Mass spectrum: M/z 249 (ES+), theoretical M=248

HPLC: column: Hypercarb® 250×4 mm Detection: 202 nm

Isocratic eluent 99/1: 0.034 N $H_2SO_4$/$CH_3CN$-Tr=8 min

Examples 2 to 7

Preparation of Biovectors

Example 2

Preparation of Compound B

1) Ethyl-2,5-dioxo-2,5-dihydro-1H-pyrrole-1-carboxylate 9.7 g (0.1 mol) of maleimide are solubilized in 50 ml of ethyl acetate and 1.1 ml of N-methylmorpholine at 5° C.

1.1 ml of ethyl chloroformate are added dropwise. The mixture is stirred for ½ hour. The insoluble material is removed by filtration. The filtrate is washed with 50 ml of water. The organic phase is dried over $MgSO_4$ and is then concentrated under vacuum. The oil obtained is purified on Merck Geduran® silica gel (40-63 μm). Elution: $CH_2Cl_2$/ACOEt 66/34.

16.9 g are isolated with a yield of 50%.

Mass spectrum: M/z=170.1 (ES+) theoretical M=169

2) tert-Butyl 3-(2,5-dioxo-2,5-dihydro-1H-pyrrol-1yl)propylcarbamate 0.515 g ($2.96 \times 10^{-3}$ mol) of compound B 1) is solubilized in 20 ml of saturated $NaHCO_3$. The solution is filtered through a filter with a porosity of 0.45 μm and is then cooled to 0° C.

0.5 g ($2.96 \times 10^{-3}$ mol) of ethylcarbonylmaleimide in solution in 25 ml of tetrahydrofuran is added dropwise. The mixture is stirred for 15 minutes.

25 ml of tetrahydrofuran are added and the reaction medium is stirred for 45 min. The pH is adjusted to 6 with qs HCl [1N]. The product is extracted with 2×200 ml of ethyl acetate. The organic phase is dried over $MgSO_4$ and is then concentrated under vacuum.

737 mg are isolated with a yield of 98%.

3) 1-(3-Aminopropyl)1H-pyrrol-2.5-dione 0.7 g ($2.75 \times 10^{-3}$ mol) of compound B 2) is stirred in 25 ml of HCl [2 N] for 24 hours.

The solution is concentrated under vacuum. 500 mg are obtained with a yield of 88%.

Mass spectrum: M/z=155.1 (ES+) theoretical M=154.1

Example 3

Preparation of Compound C

1-Deoxy-1-[(2,3-dihydropropyl)amino]hexitol 173 g (1.9 mol) of 3-amino-1,2-propanediol are solubilized in 1 liter of methanol. 360 g (2 mol) of glucose are added. The mixture is stirred for 24 hours at ambient temperature. This solution is reduced under 20 bar of hydrogen at 60° C. with 50 g of palladium-on-charcoal and 450 ml of water for 6 hours.

The reaction medium is filtered over clarcel at 35° C. The filtration liquors are concentrated to a volume of 850 ml. The concentrate is run into 3 liters of isopropyl alcohol kept at 35° C. with a bath of hot water. The precipitate is filtered off and dried under vacuum. 272 g are isolated with a yield of 53%.

Mass spectrum: M/z=256.4 (ES+) theoretical M=253.3

Example 4

Preparation of the Compound D: N-[(2,3-Dihydroxypropyl)-(2,3,4,5,6-pentahydroxyhexyl)]-2,4,6-tribromo-5-(glycylamino)isophthalamide 255 g (1.9 mol) of compound C are dissolved at 80° C. in 2.5 liters of 1-methyl-2-pyrrolidinone for 30 minutes. The reaction medium is cooled to 40° C. before the addition of 67.1 g (0.635 mol) of $Na_2CO_3$ dried at 170° C. and of 407.8 g (0.635 mol) of 5-phthalamido(acetamido)-2,4,6-triaminoisophthalic acid chloride, keeping the temperature below 45° C.

The medium is maintained at 40° C. for 2 hours and is then cooled to 20° C., before filtration of the minerals over Clarcel.

610 ml of water are added to the filtrate and the mixture is heated to 70° C. before the addition of 44.8 ml of hydrazine hydrate (0.889 mol). The reaction medium is heated at 90° C. for 2 hours.

The pH is adjusted to 1 with QS HCl [12 N]. The precipitate formed is removed by filtration. The filtration liquors are run into 30 liters of ethanol.

The product obtained is dissolved in 3.6 liters of water, the pH is adjusted to 6.5 with QS sodium hydroxide [2N] and the solution is diafiltered. HPLC monitoring of the purification. HPLC purity=98.2%.

HPLC Conditions:

Column: C18 Symetry® 250×4 mm (5 μm). Detection: 254 nm

Isocratic eluent: 99/1: $H_2SO_4$ 0.034 N/$CH_3CN$

Bromine assays=23.6% (i.e. a purity of 97.2%)

Example 5

Preparation of Compound E: N—N'-[bis(2,3,4,5,6-pentahydroxyhexyl)]-2,4,6-tribromo-5-(glycylamino)isophthalamide

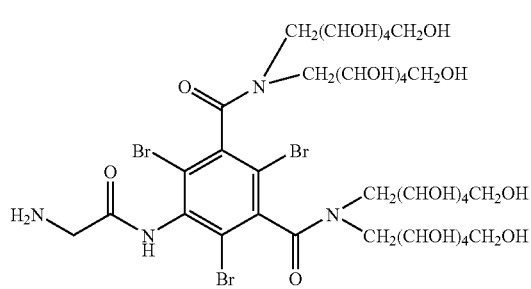

Compound E can be prepared according to the procedure described in patent: EP 0 922 700 A1.

Example 6

Preparation of Compound F: (18S)-1-amino-18{[(2-amino-4-oxo-3,4-dihydropteridin-6-yl)methyl]amino}benzoyl)amino]-15-oxo-4-trioxa-14-azanonadecan-19-oic acid

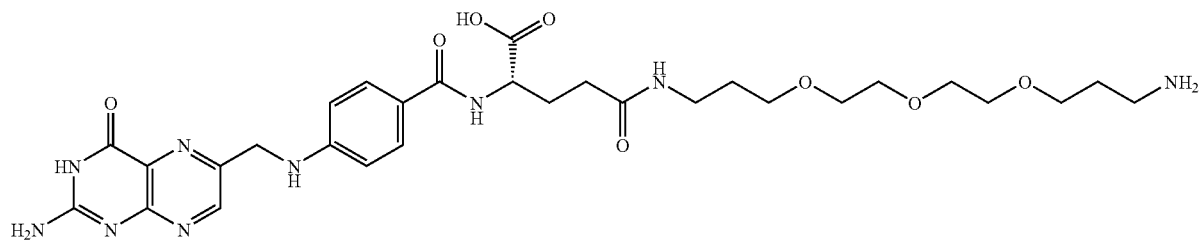

9.74 g (0.0214 mol) of (2S)-2-[(4-{[(2-amino-4-oxo-3,4-dihydropteridin-6-yl)methyl]amino}benzoyl)amino]-5-methoxy-5-oxopentanoic acid (which can be prepared according to the procedure in *J. Am. Chem. Soc.*, 1997, 119, 10004-10013) are solubilized in 60 ml of DMSO at ambient temperature. 235 ml (1.07 mol) de 4,7,10-Trioxa-1,13-tridecanediamine are added. The mixture is stirred for 48 H at ambient temperature.

The reaction medium is run into a mixture of 1.5 l of $CH_3CN$ and 1.5 l of ethyl ether. The precipitate obtained is filtered off and dried under vacuum.

The crude product is solubilized in 100 ml of pyridine [0.1 N] and is purified on 1 kg of silanized silica 60 (0.063-0.200 mm) with an elution of 9/1 pyridine [0.1 N]-methanol [HPLC monitoring]. 2.7 g are isolated with a yield of 26% and an HPLC purity of 97.3%.

HPLC Conditions:

Column: C18 Symetry® 250×4 mm (5 µm). Detection: 254 nm Isocratic eluent: 99/1: 0.034 N $H_2SO_4$/$CH_3CN$.

Example 7

Preparation of Compound G

L-Propyl-L-leucyl-$N^1$-hydroxyglycinamide 1 g ($2.3 \times 10^{-3}$ mol) of 1-[(benzyloxy)carbonyl]-L-propyl-L-leucyl-$N^1$-hydroxyglycinamide is dissolved in 100 ml of methanol.

100 mg of 50% hydrated Pd/C are added to the solution. The mixture is stirred for 6 hours at ambient temperature under 50 PSI of hydrogen.

The catalyst is removed by filtration and the filtrate is concentrated under vacuum. The product is stored at 4° C.

Quantitative yield.

Mass spectrum: M/z=371.2 (ES−) theoretical M=372.4

Examples 8 and 9

Examples of Preparation of Colloidal Solutions of Acid Magnetic Particles (p)

Example 8

A solution of 36 g (0.181 mol) of $FeCl_2 \cdot 4H_2O$ and 20 ml of HCl at 37% in 150 ml of $H_2O$ is introduced into a mixture consisting of 3 liters of water and 143 ml (0.302 mol) of $FeCl_3$ at 27%. 250 ml of $NH_4OH$ at 25% are introduced rapidly with vigorous stirring. The mixture is stirred for 30 min. The liquors are removed by magnetic separation. The ferrofluid is washed 3 times consecutively with 2 liters of water.

The nitric ferrofluid is stirred for 15 min with 200 ml of $HNO_3$ [2M], and the supernatant is removed by magnetic separation.

The nitric ferrofluid is brough to reflux with 600 ml of water and 200 ml of $Fe(NO_3)_3$ [1M] for 30 min. The supernatant is removed by magnetic separation.

The nitric ferrofluid is stirred for 15 min with 200 ml of $HNO_3$ [2M], the supernatant being removed by magnetic separation.

The nitric ferrofluid is washed 3 times with 3 liters of acetone, and is then taken up with 400 ml of water. The solution is evaporated under vacuum until a final volume of 250 ml is obtained.

| Concentration M/L | Z ave nm | Poly σ | Diameter SQUID | Ms emu/cm³ |
|---|---|---|---|---|
| 4.85 | 40 nm | 0.22 | 8.5 nm | 275 |

Ms (emu/cm³) = magnetization at saturation
Z ave = Hydrodynamic size by PCS in unimodal mode
Poly σ: peak polydispersity by PCS
SQUID = diameter of the nongrafted particle (p) estimated by deconvolution of magnetization curves measured on a SQUID magnetometer

Example 9

108 g (0.543 mol) of $FeCl_2.4H_2O$ in 450 ml of $H_2O$ is introduced into a solution of 4 liters of water and 429 ml (0.906 mol) of $FeCl_3$ at 27%. 750 ml of $NH_4OH$ at 25% are introduced rapidly with stirring (1200 rpm). The mixture is stirred for 30 min. The liquors are removed by magnetic separation. The ferrofluid is washed twice consecutively with 3 liters of water.

The nitric ferrofluid is stirred for ¼ H with 3 liters of $HNO_3$ [2M], and the supernatant is removed by magnetic separation.

The nitric ferrofluid is brought to reflux with 1300 ml of water and 700 ml of $Fe(NO_3)_3$ [1M] for 30 min (600 rpm). The supernatant is removed by magnetic separation.

The nitric ferrofluid is stirred for 15 min with 3 liters of $HNO_3$ [2M], the supernatant being removed by magnetic separation.

The nitric ferrofluid is washed 3 times with 3 liters of acetone, and is then taken up with 600 ml of water. The solution is evaporated under vacuum until a final volume of 250 ml is obtained.

At this stage, the following characteristics are obtained:

| % yield | Concentration M/L | Z ave (nm) | Poly σ |
|---|---|---|---|
| 81.8 | 4.45 | 31.3 | 0.21 |

Z ave = Hydrodynamic size by PCS in unimodal mode.

Treatment:

200 ml of the preceding solution are stirred in 2.4 liters of $HNO_3$ for 4 hours. The supernatant is removed by magnetic separation. The nitric ferrofluid is washed twice with 3 liters of acetone, and is then taken up with 400 ml of water. The solution is evaporated under vacuum until a final volume of 250 ml is obtained.

| % yield | Concentration M/L | Z ave (nm) | Poly σ |
|---|---|---|---|
| 77 | 2.742 | 23.3 | 0.20 |

Examples 10 to 12

Examples of Complexation of the Magnetic Particles (p) by Compounds of Formula (I)

Example 10

50 ml of example 8 at 4.85 M/L are diluted in 3 liters of water. A solution of 1.3 g ($5.24 \times 10^{-3}$ mol) of compound A from Example 1 in 100 ml of water is introduced dropwise. Stirring is maintained for 30 minutes. The flocculate is isolated by magnetic separation and is then washed 3 times with 3 liters of water.

It is redissolved with 700 ml of water at pH 7.2 with QS NaOH [1 N]. The final solution is filtered through a 0.22 μm membrane.

Iron titer=0.252 M/L PCS size=67.9 nm
Fe=61.7% mass/mass
P=1.21% mass/mass
C=1.04% mass/mass
Degree of grafting [compound A/Fe]=1.86% mol/mol

Example 11

50 ml of example 8 at 4.73 M/L are diluted in 3 liters of water. A solution of 1.3 g ($5.24 \times 10^{-3}$ mol) of compound A from Example 1 in 80 ml of water is introduced dropwise. Stirring is maintained for 30 minutes. The flocculate is isolated by magnetic separation and is then washed 3 times with 3 liters of water.

It is redissolved with 700 ml of water at pH 11 with QS NaOH [1N] and then stabilized at pH 7.2 with QS HCl [1N]. The final solution is filtered through a 0.22 μm membrane.

Iron titer=0.279 M/L PCS size=40.3 nm Poly σ=0.19
Fe=63.9% mass/mass
P=1.38% mass/mass
C=1.07% mass/mass
Degree of grafting [compound A/Fe]=1.95% mol/mol

Example 12

100 ml of example 9 at 2.742 M/L (PCS size=21.3 nm) are diluted in 3 liters of water.

A solution of 1.5 g ($6.03 \times 10^{-3}$ mol) of compound A from example 1 in 100 ml of water is introduced dropwise. The stirring is maintained for 30 minutes. The flocculate is isolated by magnetic separation and is then washed 3 times with 3 liters of water.

It is redissolved with 700 ml of water at pH 11 with QS NaOH [1N] and then stabilized at pH 7.2 with QS HCl [1N]. The final solution is filtered through a 0.22 μm membrane.

Iron titer=0.285 M/L PCS size=25.6 nm
Fe=62.9% mass/mass
P=1.32% mass/mass
C=1.22% mass/mass
Degree of grafting [compound A/Fe]=1.90% mol/mol Relaxivities:

20 MHz (0.47 T)—37° C.—in aqueous solution

| $r_1$ ($mM^{-1} \cdot s^{-1}$) | $r_2$ ($mM^{-1} \cdot s^{-1}$) |
|---|---|
| 35 ± 2 | 103 ± 5 |

Examples 13 to 18

Coupling of the Acid Magnetic Particles (p) Complexed by Compounds of Formula (I), with Biovectors

Example 13

36 mg ($1.88 \times 10^{-4}$ mol) of compound B are dissolved in 50 ml of example 10 at 0.252 M/L. The pH is adjusted to 5.8 with QS HCl [1N].

A drop of triethylamine and 72 mg of 1-(3-dimethylaminopropyl)-3-ethylcarbodiimide hydrochloride are added to the reaction medium and the mixture is stirred at ambient temperature for 18 hours.

The solution is ultrafiltered through a PALL® stirring cell having a cutoff threshold of 30 kD. 600 ml of filtrate are removed in order to obtain a final solution of 35 ml.

[Fe]=0.212 M/L PCS size=69.2 nm
Fe=62.8% mass/mass
P=1.21% mass/mass
C=2.23% mass/mass
N=0.48% mass/mass
Degree of grafting [compound A/Fe]=1.74% mol/mol
Degree of grafting [compound B/Fe]=1.37% mol/mol
Degree of grafting [compound B/compound A]=78.6%

Example 14

0.193 g ($7.6 \times 10^{-4}$ mol) of compound C from example 3 is dissolved in 13.55 ml of example 11 at 0.279 M/L. The pH is adjusted to 6.2.

171 mg of 1-(3-dimethylaminopropyl)-3-ethylcarbodiimide hydrochloride are added. The mixture is stirred at ambient temperature for 24 hours. The solution is ultrafiltered through a PALL® stirring cell having a cutoff threshold of 30 kD. 500 ml of filtrate are removed. The retentate is adjusted to 30 ml

[Fe]=0.155 M/L PCS size=43.7 nm
Fe=58.4% mass/mass
P=1.17% mass/mass
C=2.80% mass/mass
Degree of grafting [compound A/Fe]=1.80% mol/mol
Degree of grafting [compound C/Fe]=1.67% mol/mol
Degree of grafting [compound C/compound A]=93%

Example 15

0.358 g ($3.78 \times 10^{-4}$ mol) of compound D from example 4 are dissolved in 13.55 ml of example 11 at 0.279 M/L.

86 mg of 1-(3-dimethylaminopropyl)-3-ethylcarbodiimide hydrochloride are added. The mixture is stirred at ambient temperature for 24 hours. The solution is ultrafiltered through a PALL® stirring cell having a cutoff threshold of 30 kD. 500 ml of filtrate are removed. The retentate is adjusted to 30 ml

[Fe]=0.134 M/L PCS size=41.3 nm
Fe=51.2% mass/mass
P=1.16% mass/mass
C=5.79% mass/mass
Br=3.07% mass/mass
Degree of grafting [compound A/Fe]=2% mol/mol
Degree of grafting [compound D/Fe]=1.4% mol/mol
Degree of grafting [compound D/compound A]=68.4%

Example 16

0.853 g ($7.6 \times 10^{-4}$ mol) of compound E from example 5 are dissolved in 13.55 ml of example 11 at 0.279 M/L. The pH is adjusted to 6.2.

171 mg of 1-(3-dimethylaminopropyl)-3-ethylcarbodiimide hydrochloride are added. The mixture is stirred at ambient temperature for 24 hours. The solution is ultrafiltered through a PALL® stirring cell having a cutoff threshold of 30 kD. 500 ml of filtrate are removed. The retentate is adjusted to 30 ml

[Fe]=0.132 M/L PCS size=41.6 nm poly σ=0.22
Fe=52.3% mass/mass
P=0.77% mass/mass
C=5.86% mass/mass
Br=2.65% mass/mass
Degree of grafting [compound A/Fe]=1.33% mol/mol
Degree of grafting [compound E/Fe]=1.18% mol/mol
Degree of grafting [compound E/compound A]=89%

Example 17

90 ml of a solution containing 1.35 g/L of compound F from example 6 are introduced into 66.3 ml of example 12 at 0.285 M/L. 121.7 mg of 1-(3-dimethylaminopropyl)-3-ethylcarbodiimide hydrochloride are added. The pH is adjusted to 6.8 and the mixture is stirred at ambient temperature for 18 hours.

The reaction medium is ultrafiltered through a PALL® stirring cell having a cutoff threshold of 30 kD. The retentate is adjusted to 100 ml and is then filtered through 0.22 μm.

[Fe]: 0.213 M/L PCS size=29 nm
Fe=59.6% mass/mass
P=1.29% mass/mass
C=2.67% mass/mass
N=0.38% mass/mass
Degree of grafting [compound A/Fe]=1.95% mol/mol
Degree of grafting [compound F/Fe]=0.28% mol/mol
Degree of grafting [compound F/compound A]=14.5%

Relaxivities:
20 MHz (0.47 T)—37° C.—in aqueous solution

| $r_1$ (mM$^{-1}$·s$^{-1}$) | $r_2$ (mM$^{-1}$·s$^{-1}$) |
|---|---|
| 36 ± 2 | 105 ± 5 |

These results show that coupling of the biovector does not modify the relaxivities of the noncoupled intermediate (example 12).

Example 18

100 ml of a solution of example 12 at 0.285 M/L are ultrafiltered through a PALL® 30 KD stirring cell. 202 mg of compound G from example 7 are added to this solution. The pH is adjusted to 6.1 with QS HCl [0.1 N].

203 mg of 1-(3-dimethylaminopropyl)-3-ethylcarbodiimide hydrochloride are added and the mixture is stirred at ambient temperature for 6 hours.

The reaction medium is ultrafiltered through a PALL® stirring cell having a cutoff threshold of 30 kD. 800 ml of filtrate are removed. The retentate is adjusted to 140 ml and is then filtered through 0.22 μm.

[Fe]: 0.223 M/L PCS size=28.4 nm
Fe=57.9% mass/mass
P=1.37% mass/mass
C=3.49% mass/mass
N=0.89% mass/mass
Degree of grafting [compound A/Fe]=2.13% mol/mol
Degree of grafting [compound G/Fe]=1.5% mol/mol
Degree of grafting [compound G/compound A]=71%

Examples 19 to 21

Comparison of the Magnetic Particles Complexed by a Gem-Bisphosphonate Compound and Coupled to a Biovector, Derived from an "Alkaline" Ferrofluid Precursor, with those Derived from an "Acid" Ferrofluid Precursor Example 19

Preparation of an "Alkaline" Ferrofluid in TMAOH Medium

A mixture consisting of a solution of 2.96 ml of $FeCl_3$ at 27%, and of a solution of 0.6 g of $FeCl_2.4H_2O$ in 40 ml of water is rapidly run into 200 ml of tetramethylammonium hydroxide [1 M]. The mixture is stirred for 1 hour at ambient temperature. The solution is filtered through a 0.22 μm membrane and kept under nitrogen at 4° C.

[Fe]: 0.0403 M/L PCS size=68.2 nm Polydispersity σ=0.48

Example 20

Complexation of the "Alkaline" Ferrofluid from Example 19 by the Gem-Bisphosphonate Compound from Example 1

A solution consisting of 416 mg of compound A from example 1 in solution in 5 ml of water is introduced into 25 ml of example 19. The mixture is stirred for 1 hour and then ultrafiltered through a PALL® stirring cell having a cutoff threshold of 30 kD.

600 ml of filtrate are removed. The retentate is adjusted to 40 ml and is then filtered through a 0.22 μm membrane.

Example 21

Coupling of the Complexed Magnetic Particles from Example 20 with Compound E from Example 5

1.7 g of compound E are introduced into the 40 ml of solution from example 20. The pH is adjusted to 6.2. 345 mg of 1-(3-dimethylaminopropyl)-3-ethylcarbodiimide hydrochloride are then added and the mixture is stirred for 24 hours at ambient temperature.

The reaction medium is ultrafiltered through a PALL® stirring cell having a cutoff threshold of 30 kD.

700 ml of filtrate are removed. The retentate is adjusted to 40 ml and is then filtered through 0.22 μm.

PCS size=60 nm Polydispersity σ=0.60
Fe=37.9% mass/mass
P=1.70% mass/mass
C=12.96% mass/mass
N=1.84% mass/mass
Br=6.42% mass/mass
Degree of grafting [compound A/Fe]=4.04% mol/mol
Degree of grafting [compound E/Fe]=3.95% mol/mol
Degree of grafting [compound E/compound A]=97.7%

Precursors

|  | N° | Size Z ave (nm) | Polydispersity σ |
|---|---|---|---|
| Acid ferrofluid | Example 8 | 40 | 0.22 |
| Alkaline ferrofluid | Example 19 | 68.2 | 0.48 |

Final molecules (acid or basic ferrofluid+gem-bisphosphonate compound (Ia)+biovector compound E):

|  | N° | Size Z ave (nm) | Polydispersity σ |
|---|---|---|---|
| Acid process | Example 16 | 41.6 | 0.22 |
| Alkaline process | Example 21 | 60 | 0.60 |

Conclusions:

For examples 19 and 21, the inventors have advantageously demonstrated that, when an alkaline ferrofluid comparable to that used in document *J. of Coll. and Interf.*, Science, 2001, 238, pp. 37-42 is used, the hydrodynamic size is greater from the precursor step (alkaline ferrofluid—example 19) and the polydispersity is high (σ=0.48) compared to the acid ferrofluid (σ=0.22); this has an influence on the hydrodynamic size of the final product (after grafting of the compound 1a and of the biovector—compound E), with an even greater polydispersity (σ=0.6). The difference in % (compound A/iron) between the two types of final particles derived respectively from an acid ferrofluid or a basic ferrofluid indicates the definite formation of a double layer of compound I (gem-bisphosphonate) when an "alkaline" precursor is used, which is prejudicial to good stability. In the process according to the invention, 90% of the sites are grafted with a compound of formula (I), advantageously forming a monolayer.

Examples 22 to 25

Preparation of Other Biovectors

Example 22

Preparation of Compound H

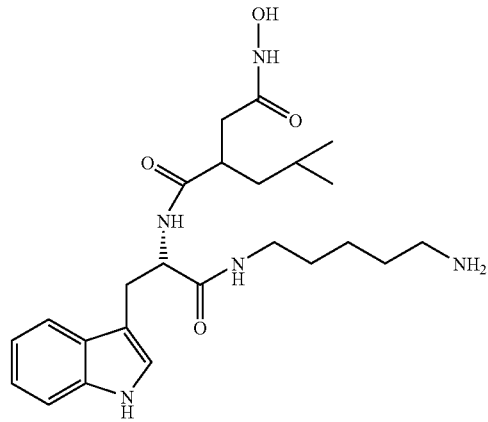

1) Benzyl 5-{[(2R)-2-{[(9H-fluoren-9-ylmethoxy)carbonyl]amino}-3-(1H-indol-3-yl)propanoyl]amino}pentylcarbamate 15.63 g of ((2R)-2-{[(9H-fluoren-9-ylmethoxy)carbonyl]amino}-3-(1H-indol-3-yl)propanoic acid) are solubilized at ambient temperature in 300 ml of tetrahydrofuran.

10 g of (benzyl-5-aminopentylcarbamate) and then 5.1 ml of triethylamine are added. The mixture is stirred for 5 minutes at ambient temperature.

5.94 g of hydroxy-1-benzotriazole hydrate and then 8.43 g of 1-(3-dimethylaminopropyl)-3-ethylcarbodiimide hydrochloride are subsequently added to the reaction medium. The mixture is stirred for 24 hours at ambient temperature.

The insoluble material is removed by filtration. The filtrate is concentrated under vacuum.

The oil obtained is run into 150 ml of water and is stirred for 1 hour at ambient temperature.

The precipitate obtained is filtered, and washed with vigorous stirring in 100 ml of water for 30 minutes at ambient temperature.

The precipitate is filtered off, then washed with 200 ml of ethyl ether, and then dried under vacuum. 22.78 g are isolated with a yield of 96.4%.

Rf=0.94 on silica (MERCK) in $CH_2Cl_2/CH_3OH$ (8/2)

HPLC: Waters C18 symmetry column, 5 µm, (250 mm×4.6 mm)

| Gradient: water-TFA (pH 2.95)/$CH_3CN$: $\lambda = 210$ nm | | | |
|---|---|---|---|
| Time in min. | Flow rate ml/min. | % water-TFA pH 2.95 | % $CH_3CN$ |
| 0 | 1 | 98 | 2 |
| 50 | 1 | 10 | 90 |
| 55 | 1 | 5 | 95 |

Retention time of the expected product: 42 min

Mass spectrum: m/z=645.3 (ES⁺ mode) (theoretical M=644)

2) Benzyl 5-{[(2R)-2-amino-3-(1H-indol-3-yl)propanoyl]amino}pentylcarbamate 20 g of (benzyl 5-{[(2R)-2-{[(9H-fluoren-9-ylmethoxy)carbonyl]amino}-3-(1H-indol-3-yl)propanoyl]amino}pentylcarbamate) are solubilized at ambient temperature in 280 ml of tetrahydrofuran.

41.4 ml of piperidine and 20 ml of water are then added. The mixture is stirred for 3 hours at ambient temperature. The reaction medium is concentrated under vacuum.

The oil obtained is purified over 1400 g of Merck Geduran® silica (40-63 µm). Elution: $CH_2Cl_2/CH_3OH$ (95/5).

12.77 g are isolated with a yield of 97.4%.

Rf=0.64 on silica (MERCK) in $CH_2Cl_2/CH_3OH$ (95/5)

HPLC: Waters C18 symmetry column, 5 µm, (250 mm×4.6 mm)

| Gradient: water-TFA (pH 2.95)/$CH_3CN$: $\lambda = 210$ nm | | | |
|---|---|---|---|
| Time in min | Flow rate ml/min | % water-TFA pH 2.95 | % $CH_3CN$ |
| 0 | 1 | 98 | 2 |
| 17 | 1 | 66 | 34 |
| 19 | 1 | 64 | 36 |
| 50 | 1 | 0 | 100 |

Retention time of the expected product: 18.2 min

Mass spectrum: m/z=423.2 (ES⁺ mode) (theoretical M=422)

3) Tert-butyl (12R)-12-(1H-indol-3-ylmethyl)-15-isobutyl-3,11,14-trioxo-1-phenyl-2-oxa-4,10,13-triazaheptadecan-17-oate 9.16 g of (2-(2-tert-butoxy-2-oxoethyl)-4-methylpentanoic acid), synthesized according to the procedure described in (J. Med. Chem. 1998, Vol 41 (2): p. 209), are solubilized at ambient temperature in 160 ml of tetrahydrofuran.

A homogeneous solution made up of 16.81 g (0.039 mol) of (benzyl 5-{[(2R)-2-amino-3-(1H-indol-3-yl)propanoyl]amino}pentylcarbamate) in 165 ml of tetrahydrofuran is added all at once, followed by, successively, 8.3 ml of triethylamine, 6.45 g of hydroxy-1-benzotriazole hydrate and 9.5 g of 1-(3-dimethylaminopropyl)-3-ethylcarbodiimide hydrochloride.

The mixture is stirred for 12 hours at ambient temperature. The insoluble material is removed by filtration. The filtrate is concentrated under vacuum.

The oil obtained is purified on 1900 g of Merck Geduran® silica (40-63 µm). Elution of the correct product with $CH_2Cl_2/CH_3OH$ (98/2).

24 g are isolated with a yield of 95.3%.

Rf=0.42 on silica (MERCK) in $CH_2Cl_2/CH_3OH$ (95/5)

HPLC: Waters C18 symmetry column, 5 µm, (250 mm×4.6 mm)

| Gradient: water-TFA (pH 2.95)/$CH_3CN$: $\lambda = 220$ nm | | | |
|---|---|---|---|
| Time in min | Flow rate (ml/min) | % water-TFA pH 2.95 | % $CH_3CN$ |
| 0 | 1 | 98 | 2 |
| 30 | 1 | 0 | 100 |

Retention time of the expected product: 25.7 min

Mass spectrum: m/z=635.6 (ES⁺ mode) (theoretical M=634)

4) (12R)-12-(1H-indol-3-ylmethyl)-15-isobutyl-3,11,14-trioxo-1-phenyl-2-oxa-4,10,13-triazaheptadecan-17-oic acid 1.4 g of dithioerythritol are added to a solution made up of 100 ml of $CH_2Cl_2$ and 100 ml of trifluoroacetic acid. 10 g of (tert-butyl (12R)-12-(1H-indol-3-ylmethyl)-15-isobutyl-3,11,14-trioxo-1-phenyl-2-oxa-4,10,13-triazaheptadecan-17-oate) are then added. The mixture is stirred for 30 minutes at ambient temperature and then concentrated under vacuum.

The oil obtained is purified on 700 g of Merck Geduran® silica (40-63 μm). Elution of the correct product with $CH_2Cl_2/CH_3OH$ (98/2).

6.19 g are isolated with a yield of 68%.

Rf=0.57 on silica (MERCK) in $CH_2Cl_2/CH_3OH$ (8/2)

HPLC: C18 Waters symmetry column, 5 μm, (250 mm×4.6 mm)

| Gradient: water-TFA (pH 2.95)/$CH_3CN$: $\lambda = 210$ nm | | | |
|---|---|---|---|
| Time in min. | Flow rate (ml/min.) | % water-TFA pH 2.95 | % $CH_3CN$ |
| 0 | 1 | 98 | 2 |
| 30 | 1 | 0 | 100 |

Retention time of the expected product: 20.8 min

Mass spectrum: m/z=579.0 (ES$^+$ mode) (theoretical M=578)

5) Benzyl (8R)-8-(1H-indol-3-ylmethyl)-11-isobutyl-7,10,13-trioxo-16-phenyl-15-oxa-6,9,14-triazahexadec-1-ylcarbamate 6.11 g of ((12R)-12-(1H-indol-3-ylmethyl)-15-isobutyl-3,11,14-trioxo-1-phenyl-2-oxa-4,10,13-triazaheptadecan-17-oic acid) are solubilized at ambient temperature in 160 ml of tetrahydrofuran. The reaction medium is cooled to 0° C.

1.69 g of O-benzylhydroxylamine hydrochloride, 3 ml de triethylamine, 1.86 g of hydroxy-1-benzotriazole hydrate and then 2.63 g of 1-(3-dimethylaminopropyl)-3-ethylcarbodiimide hydrochloride are successively added to the reaction medium and the mixture is stirred for 24 hours at ambient temperature.

The insoluble material is removed by filtration. The filtrate is concentrated under vacuum.

The oil obtained is run into 200 ml of water. The precipitate obtained is filtered off, and washed in 100 ml of water at ambient temperature.

The precipitate is filtered off and dried under vacuum.

5.7 g are isolated with a yield of 79.2%.

Rf=0.29 on silica (MERCK) in $CH_2Cl_2/CH_3CN$ (5/5)

HPLC: C18 Waters symmetry column, 5 μm, (250 mm×4.6 mm)

| Gradient: water-TFA (pH 2.95)/$CH_3CN$: $\lambda = 210$ nm | | | |
|---|---|---|---|
| Time in min | Flow rate (ml/min) | % water-TFA pH 2.95 | % $CH_3CN$ |
| 0 | 1 | 98 | 2 |
| 30 | 1 | 0 | 100 |

Retention time of the expected product: 22.7 min

Mass spectrum: m/z=684.3 (ES$^+$ mode) (theoretical M=683)

6) N$^1$-[(1R)-2-[(5-aminopentyl)amino]-1-(1H-indol-3-ylmethyl)-2-oxoethyl]-N$^4$-hydroxy-2-isobutylsuccinamide 0.32 g of (benzyl (8R)-8-(1H-indol-3-ylmethyl)-11-isobutyl-7,10,13-trioxo-16-phenyl-15-oxa-6,9,14-triazahexadec-1-ylcarbamate) is dissolved in 30 ml of methanol. A half-spatula of 50% hydrated Pd/C is added to the solution.

The mixture is stirred for 4 hours thirty minutes at ambient temperature under 50 PSI of hydrogen. The catalyst is removed by filtration over clarcel and the filtrate is concentrated under vacuum. Quantitative yield.

The product obtained is purified on 5 g of Merck silanized silica 60 gel. (63-200 μm). Elution of the expected product with $H_2O$.

0.11 g is isolated with a yield of 51%.

HPLC: C18 Waters symmetry column, 5 μm, (250 mm×4.6 mm)

| Gradient: water-TFA (pH 2.95)/$CH_3CN$: $\lambda = 220$ nm | | | |
|---|---|---|---|
| Time in min. | Flow rate (ml/min.) | % water-TFA pH 2.95 | % $CH_3CN$ |
| 0 | 1 | 98 | 2 |
| 30 | 1 | 0 | 100 |

Retention time of the expected product: 9.4 min

Mass spectrum: m/z=460.3 (ES$^+$ mode) (theoretical M=459)

Example 23

Preparation of Compound I

1) O-(2-Para-toluenesulfonylethyl)-O'-methylpolyethylene glycol 1100

16.2 g of polyethylene glycol monomethyl ether of average mass 1100 (Fluka®) are dissolved in 25 ml of dichloromethane. This solution is cooled to a temperature of 5° C.

0.4 g of triethylbenzylammonium chloride, 10.4 ml of an aqueous 30% sodium hydroxide solution and then 2.94 g of para-toluenesulfonyl chloride in solution in 15 ml of $CH_2Cl_2$ are then added at 5° C.

The reaction is continued for 24 hours at ambient temperature. The extraction of the reaction medium produces, after drying over magnesium and evaporation, 17.2 g of solid. The yield is 95%.

TLC: Merck® SiO$_2$ eluent: dichloromethane methanol: 9/1.

Detection: UV 254 nm and Draggendorf: Rf=0.4

♦ Infrared: 1356 cm$^{-1}$ (v: R—O—SO$_2$—R)

2) O-(2-Azidoethyl)-O'-methylpolyethylene glycol 1100

12.4 g of O-(2-paratoluenesulfonylethyl)-O'-methylpolyethylene glycol 1100 are dissolved at ambient temperature in 90 ml of DMF. 2 g of sodium azide are then introduced. Stirring is maintained for 18 hours at ambient temperature. Extraction of the reaction medium with: $CH_2Cl_2$ produces, after evaporation, 4.4 g of compound. The yield is 40%

TLC: Merck® SiO$_2$ eluent: dichloromethane methanol: 9/1.

Detection: UV 254 nm and Draggendorf Rf=0.39

Infrared: 2104 cm$^{-1}$ (v: N$_3$)

3) O-(2-Aminoethyl)-O'-methylpolyethylene glycol 1100

4.3 g of O-(2-azidoethyl)-O'-methylpolyethylene glycol 1100 and 0.4 g of Pd/C (5%) in solution in 100 ml of ethanol are introduced into an autoclave. The reaction is carried out under a hydrogen pressure of 2.5 bar, at 25° C., for 4 hours.

The catalyst is removed by filtration over celite. After evaporation, 3.5 g are thus isolated with a yield of 85%.

TLC: Merck® $SiO_2$ eluent: dichloromethane/methanol: 9/1.

Detection: "Primary amine" specific ninhydrin

Infrared: 3390 $cm^{-1}$ (ν $NH_2$)

Example 24

Preparation of Compound J

1) Tert-butyl 3-{2-[2-(3-aminopropoxy)ethoxy]ethoxy}propylcarbamate

A solution of 5 g di(tert-butyl) dicarbonate dissolved in 50 ml of $CH_2Cl_2$ is added, by means of a dropping funnel, to 15 g of 3-{2-[2-(3-aminopropoxy)ethoxy]ethoxy}-1-propanamine dissolved in 100 ml of $CH_2Cl_2$.

The reaction medium is stirred at ambient temperature for 18 hours and is then half-concentrated so as to be washed with water (50 ml), dried and concentrated. The solution obtained is filtered over MERCK Geduran® silica (40-63 μm) with ethyl acetate and then methanol.

4.7 g of product are obtained with a yield of 64%.

Mass spectrum: M/z=321.3 (ES+) theoretical M=320.4

TLC: Rf=0.05; Silica $SiO_2$; eluent=$CH_2Cl_2$/MeOH/$NH_4OH$ (93/7/traces)

2) Tert-butyl 16-chloro-15-oxo-4,7,10-trioxa-14-azahexadec-1-ylcarbamate 10 g of tert-butyl 3-{2-[2-(3-aminopropoxy)ethoxy]ethoxy}propyl-carbamate is dissolved in 50 ml of $CH_2Cl_2$, in a three-necked flask equipped with a bath of acetone and ice. 5-g of $K_2CO_3$ dissolved in 50 ml of water and 5 g of chloroacetyl chloride dissolved in 50 ml of $CH_2Cl_2$ are added dropwise and simultaneously, by means of a dropping funnel. During the addition, the temperature of the medium is maintained at 0° C.

When all the reagents have been added, the reaction medium is maintained with magnetic stirring, at ambient temperature for 1 hour.

The 2 phases obtained are separated and the chloromethylene phase is then washed with water until neutral pH, dried over $Na_2SO_4$, filtered, and then concentrated.

11.2 g of product are obtained with a yield of 90%.

Mass spectrum: M/z=397.4 (ES+) theoretical M=396.9

TLC: Rf=0.6; silica $SiO_2$; eluent=$CH_2Cl_2$/MeOH (9/1)

3) Tert-butyl 30-amino-15-oxo-4,7,10,21,24,27-hexaoxa-14,17-diazatriacont-1-ylcarbamate 6.8 g de 3-{2-[2-(3-aminopropoxy)ethoxy]ethoxy}propylamine are diluted in 50 ml of $CH_3CN$ in the presence of $K_2CO_3$. 3.5 g of tert-butyl 16-chloro-15-oxo-4,7,10-trioxa-14-azahexadec-1-ylcarbamate dissolved in 25 ml of $CH_3CN$ are added to this suspension by means of a dropping funnel.

The reaction medium is refluxed for 2 hours and is then placed at ambient temperature for filtration over sintered glass. The filtrate is then evaporated to dryness.

The residue obtained is dissolved in 50 ml of $CH_2Cl_2$ in order to perform washes with 4 times 20 ml of water. The chloromethylene phase is dried over $Na_2SO_4$, filtered and concentrated sufficiently to envision direct purification of Merck Geduran® silica (40-63 μm) with an elution of $CH_2Cl_2$/MeOH (50/50) (retention factor Rf=0.15).

1.8 g are obtained with a yield of 50%.

HPLC: C18 symmetry column (3.5 μm) 50×2.1 mm

| Time (min.) | Flow rate (ml/min.) | % A | % B |
|---|---|---|---|
| 0 | 1 | 98 | 2 |
| 4 | 1 | 0 | 100 |
| 5 | 1 | 0 | 100 |

Dector: UV 201 nm
Mobile phase:
A: water + TFA (pH 2.8)
B: $CH_3CN$

The expected product has a retention time=1.8 min.

Mass spectrum: M/z=581 (ES+) theoretical M=580.7

4) Tert-butyl 30-[(2-ethoxy-3,4-dioxo-1-cyclobuten-1-yl)amino]-15-oxo-4,7,10,21,24,27-hexaoxa-14,17-diazatriacont-1-ylcarbamate 0.25 g of tert-butyl 30-amino-15-oxo-4,7,10,21,24,27-hexaoxa-14,17-diazatriacont-1-ylcarbamate is dissolved in 1.5 ml of $CH_2Cl_2$. 57.5 μl of 3,4-diethoxy-3-cyclobutene-1,2-dione are added.

The reaction medium is stirred magnetically for 18 hours at ambient temperature. This intermediate is not isolated.

HPLC: C18 symmetry column (3.5 μm) 50×2.1 mm

| Time (min) | Flow rate (ml/min) | % A | % B |
|---|---|---|---|
| 0 | 1 | 98 | 2 |
| 4 | 1 | 0 | 100 |
| 5 | 1 | 0 | 100 |

Dector: UV 201 nm
Mobile phase:
A: water + TFA (pH 2.8)
B: $CH_3CN$

The expected product has a retention time of 2.30 min.

5) Tert-butyl 17-acetyl-30-[(2-ethoxy-3,4-dioxo-1-cyclobuten-1-yl)amino]-15-oxo-4,7,10,21,24,27-hexaoxa-14,17-diazatriacont-1-ylcarbamate 40.6 μl of acetic anhydride are added to the reaction medium obtained in step 4). The reaction medium is stirred at ambient temperature and is then purified directly on 5 g of Merck Geduran® silica (40-63 μm) at atmospheric pressure, with an eluent of $CH_2Cl_2$/EtOH (9/1).

0.27 g of product in the form of an oil is obtained with a yield of 60%.

Mass spectrum: M/z=748 (ES+) theoretical M=746.9

6) 1-({2-[(14-acetyl-34,34-dimethyl-16,32-dioxo-4,
7,10,21,24,27,33-heptaoxa-14,17,31-triazapentatriacont-1-yl)amino]-3,4-dioxo-1-cyclobuten-1-yl}amino)-18-[(4-{[(2-amino-4-oxo-3,4-dihydro-6-pteridinyl)methyl]amino}benzoyl)amino]-15-oxo-4,7,10-trioxa-14-azanonadecan-19-oic acid 0.16 g of tert-butyl 17-acetyl-30-[(2-ethoxy-3,4-dioxo-1-cyclobuten-1-yl)amino]-15-oxo-4,7,10,21,24,27-hexaoxa-14,17-diazatriacont-1-ylcarbamate and 0.205 g of example 6 (compound F) are solubilized in 3 ml of water.

Drops of water saturated with $Na_2CO_3$ are added to the medium so as to obtain a pH=9.2. The medium is stirred magnetically for 18 hours and is then filtered through Whatmann paper, neutralized with HCl (1N) and taken up in 15 ml of $CH_2Cl_2$.

The chloromethylene phase is washed with 1 ml of water and then dried over $Na_2SO_4$, filtered and evaporated. The residue is taken up in 10 ml of EtOH in order to be precipitated from 100 ml of $Et_2$.

0.2 g of crystals (saffron orange color) are obtained with a yield of 69%.

HPLC: C18 symmetry column (3.5 µm) 50×2.1 mm

| Time (min) | Flow rate (ml/min) | % A | % B |
|---|---|---|---|
| 0 | 1 | 98 | 2 |
| 4 | 1 | 0 | 100 |
| 5 | 1 | 0 | 100 |

Dector: UV 201 nm
Mobile phase:
A: water + TFA (pH 2.8)
B: $CH_3CN$

The expected product has a retention time of 2.40 min.

Mass spectrum: M/z=673 (z=2; ES+) theoretical M=1344.5

7) 1-({2-[(14-acetyl-30-amino-16-oxo-4,7,10,21,24,27-hexaoxa-14,17-diazatriacont-1-yl)amino]-3,4-dioxo-1-cyclobuten-1-yl}amino)-18-[(4-{[(2-amino-4-oxo-3,4-dihydro-6-pteridinyl)methyl]amino}benzoyl)amino]-15-oxo-4,7,10-trioxa-14-azanonadecan-19-oic acid 0.2 g of 1-({2-[(14-acetyl-34,34-dimethyl-16,32-dioxo-4,7,10,21,24,27,33-heptaoxa-14,17,31-triazapentatriacont-1-yl)amino]-3,4-dioxo-1-cyclobuten-1-yl}amino)-18-[(4-{[(2-amino-4-oxo-3,4-dihydro-6-pteridinyl)methyl]amino}benzoyl)amino]-15-oxo-4,7,10-trioxa-14-azanonadecan-19-oic acid is dissolved in 2 ml of trifluoroacetic acid at ambient temperature.

The reaction medium is then precipitated in 20 ml of $Et_2O$, filtered and washed thoroughly with ethyl ether.

0.18 g of crystals are obtained with a yield of 78%.
HPLC: C18 symmetry column (3.5 µm) 50×2.1 mm

| Time (min) | Flow rate (ml/min) | % A | % B |
|---|---|---|---|
| 0 | 1 | 98 | 2 |
| 4 | 1 | 0 | 100 |
| 5 | 1 | 0 | 100 |

Dector: UV 201 nm
Mobile phase:
A: water + TFA (pH 2.8)
B: $CH_3CN$

The expected product has a retention time of 1.9 min.

Mass spectrum: M/z=1245 (ES+) theoretical M=1244.4

Example 25

Preparation du compound K 1) tert-butyl 35-[(2-ethoxy-3,4-dioxo-1-cyclobuten-1-yl)amino]-3,6,9,12,15,18,21,24,27,30,33-undecaoxapentatriacont-1-ylcarbamate 0.8 g of tert-butyl 35-amino-3,6,9,12,15,18,21,24,27,30,33-undecaoxapentatriacont-1-ylcarbamate is solubilized at ambient temperature in 4 ml of EtOH. 165 µl of 3,4-diethoxy-3-cyclobutene-1,2-dione are added to this solution.

The mixture is stirred at ambient temperature for 18 hours. After evaporation of the solvent, the residue obtained is dissolved in 5 ml of $CH_2Cl_2$ so as to be purified on 30 g of MERCK Geduran® silica (4-63 µm) with an eluent made up of $CH_2Cl_2$/MeOH (95/5).

0.6 g of oil is obtained with a yield of 70%.

TLC: Rf=0.5; silica $SiO_2$; eluent=$CH_2Cl_2$/MeOH (9/1)

HPLC: C18 symmetry column (3.5 µm) 50×2.1 mm

| Time (min) | Flow rate (ml/min) | % A | % B |
|---|---|---|---|
| 0 | 1 | 98 | 2 |
| 4 | 1 | 0 | 100 |
| 5 | 1 | 0 | 100 |

Dector: UV 201 nm
Mobile phase:
A: water + TFA (pH 2.8)
B: $CH_3CN$

The expected product has a retention time of 2.78 min.

Mass spectrum: M/z=769.5 (ES+) theoretical M=768.9

2) 18-[(4-{[(2-amino-4-oxo-3,4-di hydro-6-pteridinyl)methyl]amino}benzoyl)amino]-1-({2-[(39,39-dimethyl-37-oxo-3,6,9,12,15,18,21,24,27,30,33,38-dodecaoxa-36-azatetracont-1-yl)amino]-3,4-dioxo-1-cyclobuten-1-yl}amino)-15-oxo-4,7,10-trioxa-14-azanonadecan-19-oic acid 0.3 g of tert-butyl 35-[(2-ethoxy-3,4-dioxo-1-cyclobuten-1-yl)amino]-3,6,9,12,15,18,21,24,27,30,33-undecaoxapentatriacont-1-ylcarbamate and 0.34 g of example 6 (compound F) are solubilized in 4.5 ml of water and 0.7 ml of EtOH.

The pH of the medium is increased to 9.2 with drops of $Na_2CO_3$-saturated water. The reaction medium is stirred at ambient temperature for 48 hours with the pH maintained at 9.2.

After evaporation of the ethanol, the aqueous solution obtained is purified on a "Supervarioflash®" chromatographic column system with a K026033 cartridge (RP 18; 25-40 µm), with an eluent of water/$CH_3CN$ (98/2) and a flow rate of 20 ml/min.

100 mg of product are obtained with a yield of 25%.

HPLC: C18 symmetry column (3.5 µm) 50×2.1 mm

| Time (min) | Flow rate (ml/min) | % A | % B |
|---|---|---|---|
| 0 | 1 | 98 | 2 |
| 4 | 1 | 0 | 100 |
| 5 | 1 | 0 | 100 |

Dector: UV 201 nm
Mobile phase:
A: water + TFA (pH 2.8)
B: CH$_3$CN

The expected product has a retention time of 2.40 min.
Mass spectrum: M/z=684 (z=2; ES+) theoretical M=1366.5

3) 18-[(4-{[(2-amino-4-oxo-3,4-dihydro-6-pteridinyl)methyl]amino}benzoyl)amino]-1-({2-[(35-amino-3,6,9,12,15,18,21,24,27,30,33-undecaoxapentatriacont-1-yl)amino]-3,4-dioxo-1-cyclobuten-1-yl}amino)-15-oxo-4,7,10-trioxa-14-azanonadecan-19-oic acid 0.3 g of 18-[(4-{[(2-amino-4-oxo-3,4-dihydro-6-pteridinyl)methyl]amino}benzoyl)amino]-1-({2-[(39,39-dimethyl-37-oxo-3,6,9,12,15,18,21,24,27,30,33,38-dodecaoxa-36-azatetracont-1-yl)amino]-3,4-dioxo-1-cyclobuten-1-yl}amino)-15-oxo-4,7,10-trioxa-14-azanonadecan-19-oic acid is solubilized in 0.3 ml of trifluoroacetic acid.

After stirring for 15 minutes at ambient temperature, the reaction medium is evaporated and then taken up in 30 ml of Et$_2$O.

After filtration, washing with Et$_2$O and drying, 0.29 g of product is obtained.

HPLC: C18 symmetry column (3.5 µm) 50×2.1 mm

| Time (min) | Flow rate (ml/min) | % A | % B |
|---|---|---|---|
| 0 | 1 | 98 | 2 |
| 4 | 1 | 0 | 100 |
| 5 | 1 | 0 | 100 |

Detector: UV (275 nm)
Mobile phase:
A: water + TFA (pH 2.8)
B: CH$_3$CN

The expected product has a retention time of 1.87 min.
Mass spectrum: M/z=1267 (ES+) theoretical M=1266.4

Examples 26 to 37

Coupling of the Acid Magnetic Particles (p) Complexed by Compounds of Formula (I) with Biovectors Example 26

1) 102.5 mg of compound F from example 6 are introduced into 50 ml of example 12 at 0.285 M/L. 76.6 mg of 1-(3-diethylaminopropyl)-3-ethylcarbodiimide hydrochloride are added. The pH is adjusted to 6.2 and the mixture is stirred for 18 hours at ambient temperature.

The reaction medium is directly ultrafiltered through a PALL® stirring cell having a cutoff threshold of 30 kD. The retentate is adjusted to 65 ml and is then filtered through 0.22 µm, giving solution A.

Fe=67% mass/mass
P=1.29% mass/mass
C=1.95% mass/mass
N=0.26% mass/mass
Degree of grafting [compound A/Fe]=1.74% mol/mol
Degree of grafting [compound F/Fe]=0.17% mol/mol
Degree of grafting [compound F/compound A]=9.8%.

2) 3 g of compound E from example 5 are introduced into 50 ml of solution A obtained in step 1). 600 mg of 1-(3-dimethylaminopropyl)-3-ethylcarbodiimide hydrochloride are added. The pH is adjusted to 6.2 and the mixture is stirred for 18 hours at ambient temperature.

The reaction medium is directly ultrafiltered through a PALL® stirring cell having a cutoff threshold of 30 kD. The retentate is adjusted to 40 ml and is then filtered through 0.22 µm.

[Fe]: 0.289 M/L PCS size=29.6 nm
Fe=56.6% mass/mass
P=1.1% mass/mass
C=7.27% mass/mass
N=1.1% mass/mass
Br=2.6% mass/mass
Degree of grafting [compound A/Fe]=1.75% mol/mol
Degree of grafting [compound E/Fe]=1.07% mol/mol
Degree of grafting [compound E/compound A]=61%

Example 27

36.5 mg of compound H from example 22 are introduced into 30 ml of example 12 at 0.285-M/L. The pH is adjusted to 6.2 and 18 mg of 1-(3-dimethylaminopropyl)-3-ethylcarbodiimide hydrochloride are added. The mixture is stirred for 18 hours at ambient temperature.

The reaction medium is directly ultrafiltered through a PALL® stirring cell having a cutoff threshold of 30 kD. The retentate is adjusted to 65 ml and is then filtered through 0.22 µm.

[Fe]: 0.292 M/L PCS size=32.2 nm
Fe=66.0% mass/mass
P=1.48% mass/mass
C=3.35% mass/mass
N=0.69% mass/mass
Degree of grafting [compound A/Fe]=2.02% mol/mol
Degree of grafting [compound H/Fe]=0.83% mol/mol
Degree of grafting [compound H compound A]=41%

Example 28

1) 9H-Fluoren-9-ylmethyl 6-(phosphonooxy)hexylcarbamate 1.33 ml of POCl$_3$ and 1.83 ml of triethylamine are solubilized in 9 ml of heptane. 3 g of 6-(FMOC-amino)-1-hexanol in solution in 30 ml of CH$_2$Cl$_2$ are introduced dropwise into the preceding solution, maintaining a temperature of 0° C.

The reaction medium is stirred for 1 hour at 0° C. and then for 18 heures at ambient temperature. 30 ml of water are added and the mixture is stirred for 2 hours at ambient temperature.

The organic phase is washed with water and then concentrated under vacuum. The resulting solid is taken up with water, filtered and dried.

3 g of product are obtained with a yield of 81% and an HPLC purity of 60%.

HPLC: C18 X-TERRA column (5 µm) 250×4.6 mm

| Time (min) | Flow rate (ml/min) | % A | % B |
|---|---|---|---|
| 0 | 1 | 98 | 2 |
| 30 | 1 | 2 | 98 |

Detector: UV 201 nm
Mobile phase:
A: solution of ammonium carbonate, pH = 9
B: CH$_3$CN The expected product has a retention time of 14.1 min.

2) tert-Butyl 15-[(tert-butoxycarbonyl)amino]-1-(9H-fluoren-9-yl)-12-hydroxy-3-oxo-2,11,13-trioxa-4-aza-12-phosphahexadecan-16-oate 12-oxide 3 g of 9H-fluoren-9-ylmethyl 6-(phosphonooxy)hexylcarbamate and 3.73 g of Boc-serine-OtBu are dissolved in 54 ml of pyridine. A solution of 6.49 g of triisopropylbenzenesulfochloride in 42 ml of pyridine is added dropwise. The mixture is stirred at ambient temperature for 48 hours.

30 ml of water are added and the mixture is stirred for 4 hours and is then concentrated under vacuum. The residue obtained is taken up in 100 ml of ethyl ether.

The insoluble material is removed by filtration. The filtrate is concentrated under vacuum and is then purified on silica (elution: 95% CH$_2$Cl$_2$-5% MeOH).

HPLC: C18 X-TERRA column (5 μm) 250×4.6 mm

| Time (min.) | Flow rate (ml/min.) | % A | % B |
|---|---|---|---|
| 0 | 1 | 98 | 2 |
| 30 | 1 | 2 | 98 |

Detector: UV 201 nm
Mobile phase:
A: solution of ammonium carbonate, pH = 9
B: CH$_3$CN The expected product has a retention time of 20 min.

3) tert-butyl 3-{[[(6-aminohexyl)oxy](hydroxy)phosphoryl]oxy}-2-[(tert-butoxycarbonyl)amino]propanoate 3 g of tert-butyl 15-[(tert-butoxycarbonyl)amino]-1-(9H-fluoren-9-yl)-12-hydroxy-3-oxo-2,11,13-trioxa-4-aza-12-phosphahexadecan-16-oate 12-oxide are stirred in 0.62 ml of piperidine and 3 ml of water for 12 hours at ambient temperature. The reaction medium is filtered and the crystals obtained are washed twice with 50 ml of acetonitrile and then recrystallized from 100 ml of acetonitrile.

Mass spectrum: M/z=441.3 (ES+) theoretical M=440

4) 16-(tert-butoxycarbonyl)-13-hydroxy-20,20-dimethyl-13-oxido-4,18-dioxo-1-phosphono-12,14,19-trioxa-5,17-diaza-13-phosphahenicos-1-ylphosphonic acid 106 mg of tert-butyl 3-{[[(6-aminohexyl)oxy](hydroxy)phosphoryl]oxy}-2-[(tert-butoxycarbonyl)amino]propanoate in solution in 2 ml of water are introduced into a solution of 50 mg of compound A from example 1 in 4 ml of water. The pH is adjusted to 6.2 and 60 mg of 1-(3-dimethylaminopropyl)-3-ethylcarbodiimide hydrochloride are added. The mixture is stirred for 24 hours at ambient temperature.

The product obtained is purified on Merck silanized silica 60 (63-200 μm) with elution in a gradient (water/methanol) and monitoring by HPLC.

70 mg are obtained with a yield of 52%.
Mass spectrum: M/z=671.2 (ES+) theoretical M=670

5) 17-amino-1,1,14-trihydroxy-5-oxo-2-phosphono-13,15-dioxa-6-aza-1λ$^5$, 14-diphosphaoctadecan-18-oic acid 1,14-dioxide

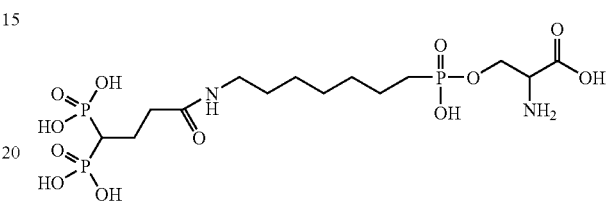

60 mg of 16-(tert-butoxycarbonyl)-13-hydroxy-20,20-dimethyl-13-oxido-4,18-dioxo-1-phosphono-12,14,19-trioxa-5,17-diaza-13-phosphahenicos-1-yl-phosphonic acid are stirred in 1 ml of TFA for 2 hours.

The solution is evaporated under vacuum and 46 mg of product are obtained with a quantitative yield.

Mass spectrum: M/z=515.1 (ES+) theoretical M=514

6) 31 mg of 17-amino-1,1,14-trihydroxy-5-oxo-2-phosphono-13,15-dioxa-6-aza-1λ$^5$, 14-diphosphaoctadecan-18-oic acid 1,14-dioxide in solution in 10 ml of water are added dropwise to a solution of 1 ml of example 9 (acid ferrofluid) at 2.742 M/L diluted in 100 ml of water. The mixture is stirred for 20 minutes at ambient temperature and the pH is adjusted to 7.2.

The solution obtained is ultrafiltered through a PALL® stirring cell having a cutoff threshold of 30 kD. 300 ml of filtrate are removed so as to obtain a final solution of 10 ml.

[Fe]=0.262 M/L PCS size=28.1 nm
Fe=67.6% mass/mass
P=1.9% mass/mass
C=3.15% mass/mass
N=0.57% mass/mass Example 29

1.75 g of compound I from example 23 are dissolved in 30 ml of example 12 at 0.285 M/L and the pH is adjusted to 6.5. 368 mg of 1-(3-dimethylaminopropyl)-3-ethylcarbodiimide hydrochloride are added. The mixture is stirred at ambient temperature for 24 hours. The solution is ultrafiltered through a PALL® stirring cell having a cutoff threshold of 30 kD. 800 ml of filtrate are removed. The retentate is adjusted to 15 ml.

[Fe]=0.496 M/L PCS size=27.1 nm
Fe=59.2% mass/mass
P=1.09% mass/mass
N=0.32% mass/mass
C=6.8% mass/mass.
Degree of grafting [compound A/Fe]=1.66% mol/mol
Degree of grafting [compound I/Fe]=0.97% mol/mol
Degree of grafting [compound I/compound A]=54%

Example 30

0.9 g of the compound O-(2-aminoethyl)-O'-methylpolyethylene glycol 750 [Amino-PEG750; Fluka] is dissolved in 22 ml of example 12 at 0.285 M/L and the pH is adjusted to 6.5. 280 mg of 1-(3-dimethylaminopropyl)-3-ethylcarbodiimide hydrochloride are added. The mixture is stirred at ambient temperature for 24 hours. The solution is ultrafiltered through a PALL® stirring cell having a cutoff threshold of 30 kD. 800 ml of filtrate are removed. The retentate is adjusted to 20 ml.

[Fe]=0.285 M/L PCS size=24.9 nm
Fe=53.2% mass/mass
P=1.30% mass/mass
N=0.35% mass/mass
C=5.87% mass/mass
Degree of grafting [compound A/Fe]=2.2% mol/mol
Degree of grafting [compound Amino-PEG750/Fe]=1.33% mol/mol
Degree of grafting [compound Amino-PEG750/compound A]=60.3%.

Example 31

3.15 g of compound O-(2-aminoethyl)-O'-methylpolyethylene glycol 2000 [Amino-PEG2000; Fluka] are dissolved in 30 ml of example 12 at 0.285 M/L and the pH is adjusted to 6.2. 368 mg of 1-(3-dimethylaminopropyl)-3-ethylcarbodiimide hydrochloride are added. The mixture is stirred at ambient temperature for 24 hours. The solution is ultrafiltered through a PALL® stirring cell having a cutoff threshold of 30 kD. 800 ml of filtrate are removed. The retentate is adjusted to 25 ml.

[Fe]=0.290 M/L PCS size=32.2 nm
Fe=46.3% mass/mass
P=1.07% mass/mass
N=0.3% mass/mass
C=10.3% mass/mass
Degree of grafting [compound A/Fe]=2.08% mol/mol
Degree of grafting [compound Amino-PEG2000/Fe]=1.07% mol/mol
Degree of grafting [compound Amino-PEG2000/compound A]=50.4%

Example 32

180 mg of compound J from example 24 are introduced into 46 ml of example 12 (concentration: 0.285 mol/L of iron) and the pH is adjusted to 6.2.

50 mg of 1-(3-dimethylaminopropyl)-3-ethylcarbodiimide hydrochloride are added to this solution. The mixture is stirred for 8 hours at ambient temperature. A further 50 mg of 1-(3-dimethylaminopropyl)-3-ethylcarbodiimide hydrochloride are added to the reaction medium and stirring is maintained for 16 hours.

The reaction medium is directly ultrafiltered through a PALL® stirring cell having a cutoff threshold of 30 kD.

The retentate is adjusted to 55 ml and is then filtered through 0.22 μm.

[Fe]: 0.273 M/L PCS size=72.4 nm
Fe=62.4% mass/mass
P=1.16% mass/mass
C=2.31% mass/mass
N=0.37% mass/mass
Degree of grafting [compound A/Fe]=1.68% mol/mol
Degree of grafting [compound J/Fe]=0.185% mol/mol
Degree of grafting [compound J/compound A]=11.0%

Example 33

750 mg of O-(2-aminoethyl)-O'-methylpolyethylene glycol 750 (Amino-PEG methyl ester 750®-Fluka) are introduced into 20 ml of example 32 at 0.273 M/L of iron and the pH is adjusted to 6.2.

200 mg of 1-(3-dimethylaminopropyl)-3-ethylcarbodiimide hydrochloride are added to the preceding solution. The mixture is stirred for 8 hours at ambient temperature. A further 200 mg of 1-(3-dimethylaminopropyl)-3-ethylcarbodiimide hydrochloride are then added to the reaction medium and stirring is maintained for 16 hours.

The reaction medium is directly ultrafiltered through a PALL® stirring cell having a cutoff threshold of 30 kD. The retentate is adjusted to 25 ml and is then filtered through 0.22 μm.

[Fe]: 0.268 M/L PCS size=69 nm
Fe=59.7% mass/mass
P=1.06% mass/mass
C=6.3% mass/mass
N=0.65% mass/mass
Degree of grafting [compound A/Fe]=1.6% mol/mol
Degree of grafting [Amino-PEG 750/Fe]=1.9% mol/mol
Degree of grafting [compound J/Fe]=0.19% mol/mol

Example 34

1.13 g of example 5 (compound E) are introduced into 20 ml of example 32 at 0.273 M/L of iron and the pH is adjusted to 6.2.

200 mg of 1-(3-dimethylaminopropyl)-3-ethylcarbodiimide hydrochloride are added to this solution. The mixture is stirred for 8 hours at ambient temperature.

A further 200 mg of 1-(3-dimethylaminopropyl)-3-ethylcarbodiimide hydrochloride are then added to the reaction mixture and stirring is maintained for 16 hours.

The reaction medium is directly ultrafiltered through a PALL® stirring cell having a cutoff threshold of 30 kD. The retentate is adjusted to 25 ml and is then filtered through 0.22 μm.

[Fe]: 0.188 M/L PCS size=79 nm
Fe=55.1% mass/mass
P=0.91% mass/mass
C=7.21% mass/mass
N=1.09% mass/mass
Br=3.08% mass/mass
Degree of grafting [compound A/Fe]=1.5% mol/mol
Degree of grafting [compound E/Fe]=1.3% mol/mol
Degree of grafting [compound J/Fe]=0.19% mol/mol

Example 35

0.29 g of compound K from example 25 is introduced into 74 ml of example 12 (concentration: 0.285 mol/L of iron) and the pH is adjusted to 6.2.

82 mg of 1-(3-dimethylaminopropyl)-3-ethylcarbodiimide hydrochloride are added to this solution and the mixture is stirred for 8 hours at ambient temperature. After 8 hours, a further 82 mg of 1-(3-dimethylaminopropyl)-3-ethylcarbodiimide hydrochloride are then added to the reaction medium and stirring is maintained for 16 hours.

The reaction medium is directly ultrafiltered through a PALL® stirring cell having a cutoff threshold of 30 kD. The retentate is adjusted to 75 ml and is then filtered through 0.22 μm.

[Fe]: 0.273 M/L PCS size=60.8 nm
Fe=63.1% mass/mass
P=1.23% mass/mass
C=4.1% mass/mass
N=0.37% mass/mass
Degree of grafting [compound A/Fe]=1.76% mol/mol
Degree of grafting [compound K/Fe]=0.22% mol/mol
Degree of grafting [compound K/compound A]=12.5%

Example 36

1 g of O-(2-aminoethyl)-O'-methylpolyethylene glycol 750 (Amino-PEG methyl ester 750®-Fluka) are introduced into 25 ml of example 35 (C=0.273 M/L of iron) and the pH is adjusted to 6.2.

274 mg of 1-(3-dimethylaminopropyl)-3-ethylcarbodiimide hydrochloride are added to this solution. The mixture is stirred for 8 hours at ambient temperature. After 8 hours, a further 274 mg of 1-(3-dimethylaminopropyl)-3-ethylcarbodiimide hydrochloride are then added to the reaction medium and stirring is maintained for 16 hours.

The reaction medium is directly ultrafiltered through a PALL® stirring cell having a cutoff threshold of 30 kD. The retentate is adjusted to 25 ml and is then filtered through 0.22 μm.

[Fe]: 0.261 M/L PCS size=59 nm
Fe=62.4% mass/mass
P=1.13% mass/mass
C=7.56% mass/mass
N=0.8% mass/mass
Degree of grafting [compound A/Fe]=1.63% mol/mol
Degree of grafting [Amino-PEG 750/Fe]=1.59% mol/mol
Degree of grafting [compound K/Fe]=0.22% mol/mol Example 37

1.61 g of example 5 (compound E) are introduced into 25 ml of example 35 (C=0.273 M/L of iron) and the pH is adjusted to 6.2.

274 mg of 1-(3-dimethylaminopropyl)-3-ethylcarbodiimide hydrochloride are added to this solution. The mixture is stirred for 8 hours at ambient temperature. After 8 hours, a further 274 mg of 1-(3-dimethylaminopropyl)-3-ethylcarbodiimide hydrochloride are then added to the reaction medium and stirring is maintained for 16 hours.

The reaction medium is directly ultrafiltered through a PALL® stirring cell having a cutoff threshold of 30 kD. The retentate is adjusted to 28 ml and is then filtered through 0.22 μm.

[Fe]: 0.240 M/L PCS size=65.6 nm
Fe=61.5% mass/mass
P=1.02% mass/mass
C=8.0% mass/mass
N=1.21% mass/mass
Br=3.8% mass/mass
Degree of grafting [compound A Fe] 1.5% mol/mol
Degree of grafting [compound E/Fe]=1.4% mol/mol
Degree of grafting [compound K/Fe]=0.22% mol/mol Assays for Affinity of the Acid Magnetic Particles (p) Complexed by Compounds of Formula (I) and Coupled with Biovectors, for Certain Biological Targets.

1/ Assay for Affinity of Example 17 for Folate Binding Protein (FBP) by the BiaCore Technique Reagents

| Products | Supplier | Reference |
|---|---|---|
| Folic acid | Avogado | 14300 |
| FBP | Sigma | F-0504 |
| Chips CM5 | BIAcore | Lots 1121065 and 11210007 |

HBS buffer: 10 mM Hepes, pH 7.4, 0.15 M NaCl, 4.3 mM EDTA and 0.005% NP20

PGM buffer: 100 mM $KH_2PO_4$, pH 7, 10% glycerol and 4 mM β-mercaptoethanol.

The immobilization of the FBP was carried out at 1 mg/ml in the PGM buffer according to the protocols recommended by BIAcore for coupling to amines. After this, the remaining active carboxylated groups are saturated with 1M of ethanolamine pH=8. The amount of FBP attached corresponds approximately to 1.5 ng/mm².

Example 17 was at a concentration of 0.170 mol/L of iron, which corresponds to $1.9\times10^{-5}$ mol of particles/L (considering a crystal of 7.5 nm, i.e. 8900 atoms of iron/particle).

The attachment of the folate was followed at four different concentrations (125, 250, 500 and 1000 μM) whereas that of example 17 was carried out at 10 μm and at 10 nM (expressed as mol of particle/L). The association and the dissociation were studied with a flow at 25 μl/min. The association and dissociation phases are 5 minutes.

Results

| Products | Association rate ka | Dissociation rate kd | Affinity constant KD |
|---|---|---|---|
| Folic acid | $10^3 M^{-1} s^{-1}$ | $1.6\ 10^{-3} s^{-1}$ | 1.6 μM |
| Example 17 | $>10^6 M^{-1} s^{-1}$ | $<10^{-6} s^{-1}$ | <1 pM |

These results demonstrate that the affinity of example 17 for folate binding protein (FBP) is very high with a lower than picomolar affinity constant KD (expressed as mol of particle/L).

Given that the folic acid receptor (represented here by FBP) is very highly overexpressed on certain tumor cells (ovarian cancer, lung cancer, colon cancer and breast cancer) and in inflammatory sites (in particular in rheumatoid arthritis), example 17 may be advantageously used as a specific MRI contrast agent in oncology and in inflammatory diseases.

2/ Inhibitory Activity of Example 27 for Human Metalloproteases MMP-1 and MMP-3.

Example 27 is covered at its surface with a biovector (example 22: compound H) derived from Ilomastat, a pseudopeptide acknowledged to be a powerful inhibitor of zinc metalloproteases (matrix metalloproteinase: MMP).

The inhibitory activity of example 27 on the human matrix metalloproteases MMP-1 and MMP-3 was evaluated in vitro. It was compared with that of example 12 (particle not functionalized with compound H) and with that of the reference peptide, Ilomastat. The protocol for measuring the inhibitory effect of the various products on MMP-1 was as follows:

Principle: evaluation of the inhibitory effect of product tested on the activity of human MMP-1 (isolated from human fibroblasts from rheumatoid synovial fluid), quantified by fluorimetry (λex=340 nm, λem=440 nm; measurement of the formation of Cys(Me)-His-Ala-Lys-(n-Me-Abz)-$NH_2$ by cleavage of the substrate DNP-Pro-Cha-Gly-Cys(Me)-His-Ala-Lys-(n-Me-Abz)-NH$_2$); protocol described in the bibliographic reference Bickett et al. (1993) *Anal. Biochem.*; 212:58.

The reference product used in this assay was GM6001 (Ilomastat, Galardin IC$_{50}$=1.9×10$^{-9}$ M).

More precisely, the test product, or the reference product or water, was added to a buffer solution, pH=7, containing 7 nM of MMP-1. The fluorescence intensity of this medium was immediately evaluated at λex=340 nm and λem=440 nm by means of a plate reader (GeminiXS, Molecular Devices). This measurement at t=0 serves to verify any possible interference of a product with the fluorescent detection. The enzyme reaction was then initiated by adding the substrate DNP-Pro-Cha-Gly-Cys(Me)-His-Ala-Lys-(n-Me-Abz)-NH$_2$ at a concentration of 10 µM. After incubation for 40 min at 37° C., the fluorescence was again evaluated under the same conditions as previously (t=40 min). The enzyme activity was determined by subtracting the signal measured at t=0 from the signal measured at t=40 min. The final result is expressed as percentage inhibition of the enzyme activity.

The protocol for measuring the inhibitory effect of the various products on MMP-3 was as follows:

Principle: evaluation of the inhibitory effect of the product tested on the activity of a human MMP-3 (use of a recombinant enzyme expressed by the sF9 cell line), quantification by fluorimetry (λex=340 nm, λem=405 nm; measurement of the formation of Mca-Arg-Pro-Lys-Pro-Tyr-Ala by cleavage of the substrate Mca-Arg-Pro-Lys-Pro-Tyr-Ala-Nva-Trp-Met-Lys(DNP)—NH$_2$ (NFF2)—protocol described in the reference: Nagase et al. (1994) *J. Biol. Chem.*; 269:20952.

The reference product used in this assay was GM6001 (Ilomastat, Galardin IC$_{50}$=1.3×10$^{-7}$ M).

More precisely, the test product, or the reference product or water, was added to a buffer solution, at pH=6, containing 6 nM of MMP-3. The fluorescence of this medium was evaluated at λex=340 nm and λem=405 nm by means of a plate reader (GeminiXS, Molecular Devices), after preincubation for 30 min at 37° C. (t=0). This measurement at t=0 serves to verify any possible interference of a product with the fluorescent detection. The enzyme reaction was then initiated by adding 10 µm of the substrate NFF-2. After incubation for 90 min at 37° C., the fluorescence was again evaluated under the same conditions as previously (t=90 min). The enzyme activity was then determined by subtracting the signal measured at t=0 from the signal measured at t=90 min.

The final result is expressed as percentage inhibition of the enzyme activity.

The results of inhibition of human MMP-1 and human MMP-3 by example 27 are given in table 1.

TABLE 1

| MMP | Concentration of iron [M] | Concentration of biovector: compound H [M] | % inhibition of the control value |
|---|---|---|---|
| MMP-1 | 1.03 × 10$^{-8}$ | 0.86 × 10$^{-10}$ | 9 |
|  | 1.03 × 10$^{-6}$ | 0.86 × 10$^{-8}$ | 86 |
|  | 1.03 × 10$^{-4}$ | 0.86 × 10$^{-6}$ | 103 |
| MMP-3 | 1.03 × 10$^{-8}$ | 0.86 × 10$^{-10}$ | 0 |
|  | 1.03 × 10$^{-6}$ | 0.86 × 10$^{-8}$ | −1 |
|  | 1.03 × 10$^{-4}$ | 0.86 × 10$^{-6}$ | 68 |

Example 27 inhibits MMP-1 at between 0.87×10$^{-10}$ and 0.87×10$^{-5}$ M (expressed as concentration of compound H), which is in agreement with the experimental value obtained for the reference peptide—Ilomastat—(IC50=1.9×10$^{-9}$ M).

Example 27 inhibits MMP-3 at between 0.87×10$^{-8}$ and 0.87×10$^{-6}$ M (expressed as concentration of compound H), which is in agreement with the experimental value obtained for the reference peptide—Ilomastat—(IC50=1.3×10$^{-7}$ M).

The results obtained with example 27 on MMP-1 and MMP-3 show that the particles of iron oxide prepared by the applicant behave in a manner very similar to the reference peptide (Ilomastat). The compound of example 27 can be used as an inhibitor with a broad spectrum with respect to metalloproteases (MMP-1, MMP2, MMP-3, MMP-7, MMP-9), and also as a specific MRI contrast agent very useful for imaging pathological regions in which these various MMPs are overexpressed.

The invention claimed is:

1. A composition consisting essentially of non-aggregated acid magnetic particles (p) based on an iron compound, the acid magnetic particles (p) being complexed by one or more gem-bisphosphonate compounds of formula I

X-L-CH(PO$_3$H$_2$)$_2$      (I)

in which
L represents an organic group connecting the X group to gem-bisphosphonate group —CH(PO$_3$H$_2$)$_2$, wherein L is
(CH$_2$)$_p$, where p is an integer from 1 to 5,
X represents a chemical group capable of reacting with a biovector and is —COOH, all or some of the X groups of the particles optionally being coupled to a biovector.

2. The composition as claimed in claim 1, in which the particles (p) are, on average, complexed on at least 90% of their protonated sites by compounds of formula (I).

3. The composition as claimed in claim 1, in which the protonated sites are complexed by at least two gem-bisphosphonate compounds of formula (I) having a different structure.

4. The composition as claimed in claim 1, in which the protonated sites are complexed by at least two compounds of formula (I) having an identical structure.

5. The composition as claimed in claim 1 in which all or some of the acid magnetic particles (p) are characterized by iron hydroxide, iron hydroxide hydrate, ferrite, mixed iron oxides or a mixture thereof.

6. The composition as claimed in claim 1, in which all or some of the acid magnetic particles (p) are characterized by a ferrite.

7. The composition as claimed in claim 6, in which the ferrite is maghemite or magnetite or a mixture thereof.

8. The composition as claimed in claim 1, in which the particles (p) are superparamagnetic.

9. The composition as claimed in claim 1, in which between 1 and 70% of the X groups of compounds of formula (I) are coupled to a biovector.

10. The composition as claimed in claim 1, in which the X groups of compounds of formula (I) are coupled to at least two different biovectors.

11. The composition as claimed in claim 1, in which the biovector is selected from proteins, optionally recombinant or mutated, glycoproteins, lectins, biotin, vitamins, phospholipids, folic acid derivatives, antibodies or antibody fragments, peptides and derivatives thereof, monosaccharides or polysaccharides, avidin, streptavidin, receptor substrates or inhibitors, steroids and analogs thereof, oligonucleotides, ribonucleic acid sequences, deoxyribonucleic acid sequences, hormones or hormone-like substances, amino acids and derivatives, organic molecules with pharmacological activity, amino alcohols, integrin-targeting agents and MMP-targeting agents.

12. The composition as claimed in claim 1, in which the biovector represents a peptide derivative.

13. The composition as claimed in claim 1, in which the X groups form a covalent bond with the biovector, of type —CONH—, —COO—, —CO—NH—N—, —CO—CH$_2$—S—, —CH=NH—NH—, —CH=N—O— and also the formulae below

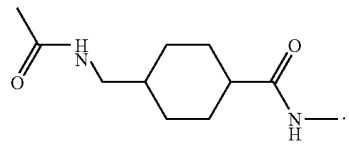

14. The composition as claimed in claim 1, in which the particles complexed and coupled to the biovector(s) have an overall hydrodynamic diameter of between 5 nm and 200 nm.

15. The composition as claimed in claim 1, in which the concentration of the particles (p) in the composition is between 2 µmol L$^{-1}$ and 4 mol L$^{-1}$, expressed as total number of moles of metal ions.

16. The composition as claimed in claim 1, further consisting essentially of one or more pharmaceutically acceptable vehicle(s) and/or additive(s).

17. The composition as claimed in claim 1, which is sterile.

18. A contrast product for magnetic resonance imaging, comprising a composition as claimed in claim 1, combined with an acceptable vehicle.

19. The composition according to claim 1 wherein the biovector is an amino alcohol.

20. The composition of claim 19, wherein the amino alcohol is N-N'-[bis(2,3,4,5,6-pentahydroxyhexyl)]-2,4,6-tribromo-5-(glycylamino)isophthalamide or N-[(2,3-dihydroxy-propyl)-(2,3,4,5,6-pentahydroxyhexyl)]-2,4,6-tribromo-5-(glycylamino)isophthalamide.

21. A process for the preparation of a composition comprising iron-based, acid magnetic particles (p) complexed by one or more gem-bisphosphonate compounds of formula I

 X-L-CH(PO$_3$H$_2$)$_2$ (I)

in which
L represents an organic group connecting the X group to gem-bisphosphonate group —CH(PO$_3$H$_2$)$_2$, wherein L is
(CH$_2$)$_p$, where p is an integer from 1 to 5,
X represents a chemical group capable of reacting with a biovector and is —COOH, all or some of the X groups of the particles optionally being coupled to a biovector,
the process comprising the successive steps of:
i) preparing a colloidal solution of acid ferrofluid by a method comprising
a) bringing an aqueous solution containing Fe$^{2+}$ and Fe$^{3+}$ salts in suitable proportions into contact with a basic solution to obtain an intermediate and
b) contacting the intermediate with an acid solution having a pH≦3, thereby forming a colloidal solution of acid ferrofluid containing iron-based, acid magnetic particles (p),
ii) contacting the colloidal solution of acid ferrofluid containing iron-based, acid magnetic particles (p) with the one or more gem-bisphosphonate compounds of formula I in sufficient amount to obtain the complexed particles, and
iii) recovering the complexed particles;
and optionally
iv) coupling all or some of the X groups of the compounds of formula (I) complexed at the surface of the magnetic particles (p) with a biovector.

22. The process of claim 21, wherein the acid solution, in step b), has pH 1-3.

23. The composition obtained by the process of claim 21.

24. The composition obtained by the process of claim 21, wherein the magnetic particles (p) are, on average, complexed on at least 90% of their protonated sites by compounds of formula (I).

25. The composition obtained by the process of claim 21, wherein the protonated sites are complexed by at least two gem-bisphosphonate compounds of formula (I) having a different structure.

26. The composition obtained by the process of claim 21, wherein the protonated sites are complexed by at least two compounds of formula (I) having an identical structure.

27. The composition obtained by the process of claim 21, wherein all or some of the magnetic particles (p) are particles of iron hydroxide, iron hydroxide hydrate, ferrite, mixed iron oxides, or a mixture thereof.

28. The composition obtained by the process of claim 21, wherein all or some of the magnetic particles (p) are ferrite particles.

29. The composition obtained by the process of claim 21, wherein all or some of the magnetic particles (p) are ferrite particles, wherein the ferrite is maghemite or magnetite or a mixture thereof.

30. The composition obtained by the process of claim 21, wherein the magnetic particles (p) are superparamagnetic.

31. The composition obtained by the process of claim 21, wherein between 1 and 70% of the X groups of compounds of formula (I) complexed at the surface of the magnetic particles (p) are coupled to a biovector.

32. The composition obtained by the process of claim 21, wherein the X groups of compounds of formula (I) complexed at the surface of the magnetic particles (p) are coupled to at least two different biovectors.

33. The composition obtained by the process of claim 21, wherein the X groups of compounds of formula (I) complexed at the surface of the magnetic particles (p) are coupled to a biovector, wherein the biovector is selected from the group cocsisting of proteins, recombinant proteins, mutated proteins, glycoproteins, lectins, biotin, vitamins, phospholipids, folic acid derivatives, antibodies and antibody fragments, peptides and derivatives thereof, monosaccharides and polysaccharides, avidin, streptavidin, receptor substrates and inhibitors, steroids and analogs thereof, oligonucleotides, ribonucleic acid sequences, deoxyribonucleic acid sequences, hormones and hormone-like substances, amino acids and derivatives, organic molecules with pharmacological activity, amino alcohols, integrin-targeting agents, and MMP-targeting agents.

34. The composition obtained by the process of claim 21, wherein the X groups of compounds of formula (I) complexed at the surface of the magnetic particles (p) are coupled to a biovector, wherein the biovector is a peptide derivative.

35. The composition obtained by the process of claim 21, wherein the X groups of compounds of formula (I) complexed at the surface of the magnetic particles (p) are coupled to a biovector, wherein the biovector is selected from the group cocsisting of —CONH—, —COO—, —CO—NH—

N—, —CO—CH₂—S—, —CH=NH—NH—, —CH=N—O—, and the formulae

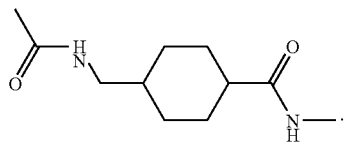

36. The composition obtained by the process of claim 21, wherein the X groups of compounds of formula (I) complexed at the surface of the magnetic particles (p) are coupled to a biovector, wherein the particles have an overall hydrodynamic diameter of between 5 nm and 200 nm.

37. The composition obtained by the process of claim 21, wherein the concentration of the magnetic particles (p) in the composition is between 2 µmol $L^{-1}$ and 4 mol $L^{-1}$, expressed as total number of moles of metal ions.

38. The composition obtained by the process of claim 21, wherein the composition further comprises one or more pharmaceutically acceptable vehicles and/or additives.

39. The composition obtained by the process of claim 21, wherein the composition is sterilized.

40. The composition obtained by the process of claim 21, wherein the X groups of compounds of formula (I) complexed at the surface of the magnetic particles (p) are coupled to a biovector, wherein the biovector is N-N'-[bis(2,3,4,5,6-pentahydroxyhexyl)]-2,4,6-tribromo-5-(glycylamino)isophthalamide.

* * * * *